(12) United States Patent
Beckler Andersen et al.

(10) Patent No.: US 9,523,103 B2
(45) Date of Patent: Dec. 20, 2016

(54) APPARATUS AND PROCESS FOR FERMENTATION OF BIOMASS HYDROLYSATE

(71) Applicant: GeoSynFuels, LLC, Golden, CO (US)

(72) Inventors: Lisa Beckler Andersen, Lakewood, CO (US); John H. Evans, IV, Superior, CO (US); Christine A. Singer, Lakewood, CO (US)

(73) Assignee: GeoSynFuels, LLC, Golden, CO (US)

( * ) Notice: Subject to any disclaimer, the term of this patent is extended or adjusted under 35 U.S.C. 154(b) by 0 days.

(21) Appl. No.: 14/717,824

(22) Filed: May 20, 2015

(65) Prior Publication Data
US 2015/0252387 A1 Sep. 10, 2015

Related U.S. Application Data

(63) Continuation of application No. 13/869,842, filed on Apr. 24, 2013, now abandoned, which is a continuation of application No. 12/856,566, filed on Aug. 13, 2010, now abandoned.

(60) Provisional application No. 61/233,821, filed on Aug. 13, 2009.

(51) Int. Cl.
| C12P 7/14 | (2006.01) |
| C12P 7/06 | (2006.01) |
| C12N 11/10 | (2006.01) |
| C12P 7/10 | (2006.01) |

(52) U.S. Cl.
CPC .............. *C12P 7/06* (2013.01); *C12N 11/10* (2013.01); *C12P 7/065* (2013.01); *C12P 7/10* (2013.01); *C12P 7/14* (2013.01); *Y02E 50/16* (2013.01)

(58) Field of Classification Search
None
See application file for complete search history.

(56) References Cited

U.S. PATENT DOCUMENTS

| 70,485 A | 11/1867 | Tilghman |
| 4,359,534 A | 11/1982 | Kurtzman et al. |
| 2,405,861 A | 8/1983 | Tod |
| 4,401,514 A | 8/1983 | Kanzler |
| 4,436,586 A | 3/1984 | Elmore |
| 4,475,984 A | 10/1984 | Cael |
| 4,477,569 A | 10/1984 | Schneider et al. |
| 4,612,286 A | 9/1986 | Sherman et al. |
| 4,996,150 A | 2/1991 | Joung et al. |
| 5,366,558 A | 11/1994 | Brink |
| 5,395,455 A | 3/1995 | Scott et al. |
| 5,589,033 A | 12/1996 | Tikka et al. |
| 5,700,684 A | 12/1997 | Ehret |
| 6,139,746 A | 10/2000 | Koph |
| 6,645,488 B2 | 11/2003 | Xue et al. |
| 6,692,578 B2 | 2/2004 | Schmidt et al. |
| 7,101,996 B2 | 9/2006 | Skuratowicz |
| 7,198,695 B2 | 4/2007 | Kettenbach et al. |
| 7,270,472 B2 | 9/2007 | Carreras |
| 7,344,876 B2 | 3/2008 | Levine |
| 7,455,997 B2 | 11/2008 | Hughes |
| 7,520,958 B2 | 4/2009 | Tan et al. |
| 7,520,988 B2 | 4/2009 | Pahl et al. |
| 7,531,344 B2 | 5/2009 | Pierce et al. |
| 7,666,637 B2 | 2/2010 | Nguyen |
| 7,785,379 B2 | 8/2010 | Drisdelle et al. |
| 8,227,219 B2 | 7/2012 | Davis |
| 2004/0203115 A1 | 10/2004 | Giardina et al. |
| 2005/0238746 A1 | 10/2005 | Crather et al. |
| 2006/0014260 A1 | 1/2006 | Fan et al. |
| 2006/0035355 A1* | 2/2006 | Ohara ............... C13B 10/00 435/161 |
| 2006/0094033 A1 | 5/2006 | Abulencia et al. |
| 2007/0086986 A1 | 4/2007 | Vigo et al. |
| 2007/0172846 A1 | 7/2007 | Zhang et al. |
| 2007/0190629 A1 | 8/2007 | Wahlbom et al. |
| 2009/0155238 A1 | 6/2009 | Weiner et al. |
| 2009/0181433 A1 | 7/2009 | Chotani et al. |
| 2009/0311765 A1 | 12/2009 | Maguire et al. |
| 2011/0056126 A1 | 3/2011 | Harvey et al. |
| 2011/0171709 A1 | 7/2011 | Bardsley |

FOREIGN PATENT DOCUMENTS

| CN | 101255446 | 9/2008 |
| JP | 58013391 A | 1/1983 |
| WO | 8203874 | 11/1982 |

OTHER PUBLICATIONS

Kastner "Oxygen starvation induces cell death in Candida shehatae fermentation of D-xylose but not D-glucose" Applied Microbiology and Biotechnology, 1999, 51, 780-785.*
Chandel "Dilute Acid Hydrolysis of Agro-Residues for the Depolymerization of Hemicellulose State of the Art" Chapter 2, D-Xylitol, Springer-Verlag, Berlin Heidelberg 2012, 39-61.*
Ohgren "A comparison between simultaneous saccharification and fermentation and separate hydrolysis and fermentation using steam pretreated corn stover" Process Biochemistry 42 (2007), 834-839.*
Li ("Fermentation of corn stalk hydrolysate by co-immobilized multi-microorganisms" Beijing Huagong Daxue Xuebao—Journal of Beijing University of Chemical Technology, 2008 vol. 35, 74-77/IDS submitted, Translation of hydrolysis conditions provided by Google Translate attached).*
About.com Chemistry, Chemostat Bioreactor, Accessed online Oct. 16, 2012 at: chemistry.about.com/od/sciencefairprojects/ig/Science-Fair-Project-Pictures/Chemostat-Bioreactor.-Lmj.htm.
Park et al., "Microencapsulation of Microbial Cells," Biotechnology Advances 18: 303-319 (2000).
Talebnia, "Ethanol Production from Cellulosic Biomass by Encapsulated *Saccharomyces cerevisiae*," Thesis for the Degree of Doctor of Philosophy, Chalmers University of Technology, Goteborg, Sweden (2008).
Zahka et al., "Practical Aspects of Tangential Flow Filtration in Cell Separations, In Purification of Fermentation Products"; LeRoith, et al. ACS Symposium Series; American Chemical Society: Washington, DC (1985).
Fredrick et al., "Co-production of Ethanol and Cellulose Fiber from Southern Pine: A Technical and Economic Assessment," 32 Biomass and Bioenergy 1293-1302 (2008).

(Continued)

*Primary Examiner* — Robert Yamasaki
*Assistant Examiner* — Charles Zoltan Constantine
(74) *Attorney, Agent, or Firm* — Sheppard Mullin Richter & Hampton LLP

(57) ABSTRACT

A process for converting biomass hydrolysate into biofuel, the process comprising the steps of: obtaining a biomass hydrolysate solution comprising monosaccharides; immobilizing *Pachysolen tannophilus*; contacting the solution with the immobilized *Pachysolen tannophilus*; and recovering a fermented biofuel.

1 Claim, 7 Drawing Sheets

(56) References Cited

OTHER PUBLICATIONS

Nagashima et al., "Continuous Ethanol Fermentation Using Immobilized Yeast Cells," Biotechnology and Bioengineering, vol. 26, 992-997 (1984).

Velez et al. "Use of Tangential Flow Filtration in Perfusion Propagation of Hybridome Cells for Production of Monocional Antibodies," Biotechnology and Bioengineering, vol. 33, 938-940 (1989), entire document.

Frederick, et al., "Ethanol and Fiber Co-Production from a Forest Biorefinery," Jul. 31, 2006 Presentation, Georgia Tech, IPST, Jyvaskyla.

Lohmeier-Vogel, et al., "Intracellular Acidification as a Mechanism for the Inhibition by Acid Hydrolysis-Derived Inhibitors of Xylose," Journal of Industrial Microbiology & Biotechnology (1998) 20, 75-81.

Davis, "What is Immobilization and the IMBR?," Jul. 27, 2009 Snapshot of screen to presentation, TMD Technologies in Spartanburg, S.C., http://www.tmd-technologies.com/index.php?option=com_content&view=article&id=49&itemid=47.

Cellulosic Biomass—Properties and Characteristics, PDF of Jul. 31, 2009, Cellulosic Biomass—Properties and Characteristics—ZERO, pp. 1-4.

U.S. Dept. of Energy, "Energy Efficiency and Renewable Energy," Industrial Technologies Program Brochure, Oct. 2006, Full Award#: FC36-04GO14306 www.eere.energy.gov/industry.

Van Neiningen, et al., "Integrated Forest Products Refinery (IFPR)", Apr. 5, and 6, 2006, ITP Peer Review Meeting Presentation, Atlanta, GA.

U.S. Dept. of Energy, "Forest Products Industry of the Future," Quarterly Status Report, as of Mar. 31, 2007.

Gavrilescu, Dan, "Energy From Biomass in Pulp and Paper Mills," Sep./Oct. 2008, vol. 7, No. 5, 537-54, Environmental Engineering and Management Journal, Gheorghe Asachi, Technical university of Iasi, Faculty of Chemical Engineering and Envrionmental Protection, 71 Mangeron Blvd., 700050, Iasi, Romania.

U.S. Dept. of Agriculture, "Pulp Yields for Various Process and Wood Species," Reissued May 1980, FPL-031, Forest Products Laboratory, Forest Service U.S. Department of Agriculture.

Toma et al., "Ultrasonically Assisted Conversion of Lignocellulosic Biomass to Ethanol," Friday, Nov. 17, 2006, 3:15 pm, Forest Products Division, Graduate School of Engineering, Department of Material Science, Osaka Prefecture University, 1-1 Gakuen-cho, Sakai, Osaka, 599-8531, Japan, Mircea Vinatoru, Sonochemistry, Institute of Organic Chemistry, Splaiul Independentei 202B, Bucharest, Romania, and Yasuaki Maeda, Department of Materials Science, Osaka Prefecture university, 1-1 Gakuen-cho, Sakai, Osaka, 599-8531, Japan.

Shin et al., "Enzymatic Extraction of Wood Hemicellulose," Friday, Nov. 17, 2006, 3:40pm, Forest Products Division, School of Chemical and Biomolecular Engineering, Georgia Institute of Technology, 778 Atlantic Dr., Atlanta, GA 30332.

Frederick, Jr. et al., "Ethanol Production from Hemicellulose Extracted from Southern Pine," Friday, Nov. 17, 2006, 4:05pm, Forest Products Division, (1) School of Chemical & Biomolecular Engineering, Georgia Institute of Technology, 500 Tenth St. NW, Atlanta, GA 30332-0620, (2) IPST, Georgia Institute of Technology, 500 Tenth Street NW, Atlanta, GA 30332-0620, (3) Georgia Institute of Technology, IPST, 500 Tenth Street NW, Atlanta, GA 30332-0620, (4) School of Chemistry & Biochemistry, Georgia Institute of Technology, 500 Tenth Street NW, Atlanta, GA 30332-0620.

Pylkkanen, Vesa A., "Value Added Pulping," Friday, Nov. 17, 2006—4:30pm, Forest Products Division, Process Integration, American Process, Inc., 56 17th Street, Atlanta, GA 30309 and Theodora Retsina, President, American Process Inc., 56 17th Street, Atlanta, GA 30309.

Connolly, Sean T., "Carbon Dioxide Gasification of Kraft Black Liquor Char in a Char Bed Reactor," Friday, Nov. 17, 2006, 4:55pm, Forest Products Division, Albert Co., and Adriaan van Heiningen, Chemical and Biological Engineering, University of Main, 301 Jenness Hall, Orono, ME 04469.

Young et al., "Pressure Effects on the Physical Cha5racteristics of High Heating Rate Black Liquor Pyrolysis and Gasification Chars," Friday, Nov. 17, 2006—5:20pm, Forest Products Division, School of Chemical & Biomolecular Engineering, Georgia Institute of Technology, 500 Tenth Street NW, Atlanta, GA 30332-0620.

Frederick, Jr. et al., "Process Design Considerations When Selecting a Black Liquor Gasifier," Friday, Nov. 17, 2006—2:35pm, Forest Products Division, (1) School of Chemical Ô Biomolecular Engineering, Georgia Institute of Technology, 500 Tenth St NW, Atlanta, GA 30332-0620, (2) IPST, Georgia Institute of Technology, 500 Tenth St. NW, Atlanta, GA 30332-0620.

Anand et al., "Evaluating Biorefinery Options in a Pulp and Paper Mill: Carbon Balances," Date Unknown, (1) School of Chemical & Biomolecular Engineering, Georgia Institute of Technoloyg, Atlanta, GA, (2) Institute of Paper Science & Technology, Georgia Institute of Technology, Atlanta, GA.

Paredes Heller et al., "Influence of Hemicellulose Extraction on Physical and Mechanical Behavior of OSB," Jun. 11, 2007—PowerPoint,FPS 61st International Convention Knoxville, TN.

Pu, Ragauskas, "Hemicellulose Pre-Extraction for Fluff Kraft Pulp Production." Unknown Date, Project, Institute of Paper Science and Technology.

Villarreal et al., "Detoxification procedures of eucalyptus hemicellulose hydrolysate for xylitol production by Candida guilliermondii". Enzyme and Microbial Technology 2006, vol. 40, pp. 17-24, see p. 18, section 2.3.

Ravinder "Fermentation of Wheat Straw Hydrolyzate to Ethanol by Pachysolen tannophilus: A comparision of Batch and Continuous Culture Systems" Biological Wastes, 30, 1989 301-308.

Slininger "Continuous Fermentation of Feed Streams Containing D-Glucose and D-Xylose in a Two-Stage Process Utilizing Immobilized Saccharomyces cerevisiae and Pachysolen tannophilus" Biotechnology and Bioengineering vol. 32 1988 1104-1112.

Gottschalk "The effect of Temperature of the Fermentation of d-Mannose by Yeast", Biochemical Journal 1947, vol. 41(2) 276-280.

Liu "draft Genome Sequence of the Yeast Pachysolen tannophilus CBS 4044/NRRL Y-2460" Eukaryotic Cell 2012 11(6) 827.

Abbi et al Bioconversion of Pentose Sugars to Ethanol by Free and Immobilized Cells of Candida shehatae (NCL-3501): Fermentation Behavoiur. Process Biochemistry vol. 31 No. 6 1996, 555-560.

Li "Fermentation of corn stalk hydrosylate by co-immobilized multi-microorganisms" Beijing Huagong Daxue Xuebao—Journal of Beijing University of Chemical Technology, 2008 vol. 35, 74-77.

Derwent abstract of Noguchi, JP 58-013391.

Smidsrod "Alginate as immobilization matrix for cells" Trends in Biotechnology, vol. 8, 1990, 71-78.

Grizzi "Calcium Alginate Dressing—I. Physico-chemical characterization and effect of sterilization" Journal of Biomaterials Science. Polymer Edition. vol. 9 Issue 2 1998, 189-204.

Schwarts "Desalting and Buffer Exchange by Dialysis, Gel Filtration, or Diafiltration" Pall Corporation, available online at www.pall.com/main/Laboratory/Literature-Library-Details.page?id.

42217, capture of google search indicating the reference has been available since 2004 included.

Uemure "Effect of Calcium Alignate coating on the performance of Immobilized Yeast cells in calcium alginate beads" Chemical Engineering Communications, vol. 177 issue 1, 2000, 1-14.

Nowak "Comparison of Polish Industrial Distillery Yeast with Ethanol Producing Zymomonas Mobilis" Electronic Journal of Polish Agricultural Universities, 2001, vol. d 4 Issue 2, online pp. 1-12.

Slininger "Continuous Conversion of D-Xylose to Ethanol by Immobilized Pachysolen tannophilus" Biotechnology and Bioengineering, vol. 24, 1982, 2241-2251.

Wooley "A Nine-Zone Simulating Moving Bed for the Recovery of Glucose and Xylose from Bimass Hydrolyzate" Industrial and Engineering Chemistry Research, 1998, 37, 3699-3709.

Gomez et al "Influence of the extraction-purification conditions on final properties of alginates obtained from brown algae" International Journal of Biological Macromolecules 44 (2009) 365-371.

(56) References Cited

OTHER PUBLICATIONS

Purwadi et al "The performance of serial bioreactors in rapid continuous production of ethanol from dilute-acid hydrolyzates using immobilized cells" School of Engineering, University of Boras (200), 2226-2233.
Junter et al "Immobilized viable microbial cells: from the process to the proteome . . . or the cart before the horse" Biotechnology Advances, 22 (2004) 633-658.
Basta et al. "Standard Technical Procedures for Microencapsulation of Human Islets for Graft into Nonimmunosuppressed Patients With Type 1 Diabetes Mellitus", Elsevier Inc., pp. 1156-1157, 2006.
Database WPI Week 200881, Thompson Scientific, London, GB; AN 2008-N85271 XP002715750.

\* cited by examiner

APPARATUS AND PROCESS FOR FERMENTATION OF BIOMASS HYDROLYSATE

This application is a Continuation of application Ser. No. 13/869,842, filed Apr. 24, 2013, which is a Continuation of application Ser. No. 12/856,566, filed Aug. 13, 2010, which claims the benefit of U.S. Provisional Application No. 61/233,821, filed Aug. 13, 2009, which are hereby incorporated by reference.

FIELD

The present patent document relates to an apparatus and process for fermentation of biomass hydrolysate.

BACKGROUND

Recently, conversion of biomass through saccharification and fermentation into ethanol or other useful products as a replacement for fossil fuels has garnered considerable attention. Because biomass is a renewable resource typically rich in polymers of hexoses and pentoses, it is a promising substrate for fermentation.

Biomass for such conversion processes may be potentially obtained from numerous different sources, including, for example: wood, paper, agricultural residues, food waste, herbaceous crops, and municipal and industrial solid wastes to name a few.

Biomass is made up primarily of cellulose and hemicellulose bound up with lignin. The lignin inhibits the conversion of the biomass into ethanol or other biofuels, and, as a result, typically a pretreatment step is required to expose the polysaccharides, cellulose and hemicellulose. Once hemicellulose and cellulose are exposed, saccharification, either enzymatic or chemical, may be performed to break the polysaccharides into their constituent monosaccharide monomers. Pretreatment and saccharification are used, therefore, to break down the long polysaccharide chains and free the sugars before they are fermented for biofuel production. Fermentation can begin once free sugars are present, either because they are naturally present or because a portion of the biomass has been reduced to its component sugars, or both.

In order to be effective, current pretreatment and saccharification processes attempt to liberate the biomass sugars while also minimizing the formation of secondary products from the degradation of hemicellulose, cellulose, and lignin, because of the inhibitory effects secondary products may have on the subsequent fermentation processes. The presence of inhibitory secondary products has historically complicated ethanol production and increased the cost of production due to elaborate detoxification steps.

Although numerous techniques for pretreatment and saccharification exist, the most popular methods, and the most cost effective methods, including acid hydrolysis, produce secondary products in addition to sugars, that are inhibitory to fermentation. Inhibitory secondary products created as a result of the degradation of hemicellulose pentoses and hexoses include furfural and 5-hydroxymethylfurfural (HMF), respectively. Furfural and HMF may further be broken down into levulinic, acetic, and formic acids. Other inhibitory secondary products include phenolic compounds produced from the degradation of lignin and acetic acid produced by cleavage of acetyl groups within the hemicellulose. Concentrations of inhibitory secondary products in the hydrolysate will vary based on the source of the biomass and the hydrolysis method used.

Some of the secondary products formed from the breakdown of hemicellulose, cellulose and lignin are in themselves valuable substances. The inventors have realized that recovery of high-value secondary products from the hydrolysate can improve the economics of the biomass to biofuel process.

Other secondary products are not formed from chemical decomposition, but may be extracted from the biomass during pretreatment and hydrolysis. These extracted secondary products include terpenes, sterols, fatty acids, and resin acids. These extracted compounds may also be inhibitory to fermentation.

Inhibitory secondary products may be detrimental to the fermentation process, particularly as their concentration increases. Thus, it would be advantageous if a process could be developed that allows specific microbes, like yeast for example, to efficiently convert biomass hydrolysate into biofuels, such as ethanol, in the presence of inhibitory secondary products formed during pretreatment and hydrolysis.

Many inhibitory products have compound impacts when present with other inhibitory compounds; thus, a non-inhibitory amount of a certain compound may become inhibitory in the presence of a second inhibitory compound. Furthermore, even following partial recovery and/or removal of inhibitory secondary products, the remaining concentrations may be inhibitory to fermentation due to these synergies. Thus, it would be advantageous if a process could be developed that allows specific microbes, like yeast for example, to efficiently convert biomass hydrolysate into biofuels, such as ethanol, in the presence of inhibitory secondary products formed during pretreatment and hydrolysis, even when the concentrations of the individual inhibitory secondary products are below their respective inhibitory concentration level but their combined concentration is inhibitory.

Cellulose is a homogeneous polysaccharide composed of linearly linked glucose units. Glucose is a hexose, which may be readily fermented by a number of microbes including *Saccharomyces cerevisiae* (traditional baker's yeast) and *Kluyveromyces marxianus*. Yeast cells are especially attractive for cellulosic ethanol processes, as they have been used in biotechnology for hundreds of years, are tolerant to high ethanol and inhibitor concentrations, and can grow at low pH values. A low pH value helps avoid bacterial contamination and is therefore advantageous.

Unlike cellulose, hemicellulose is a heterogeneous polymer of pentoses, hexoses, and uronic acids. The saccharides principally found in hemicellulose are the pentoses xylose and arabinose and the hexoses glucose, mannose and galactose. The relative amounts of different pentoses and hexoses vary with the biomass type. The hemicellulose content of some cellulosic biomass may reach as high as 38% or more of the total dry biomass weight. Therefore, hemicelluloses, and the pentoses and hexoses they contain, may comprise a substantial portion of the convertible sugars available in the biomass. As a result, in order to improve the economics of the biomass to biofuel conversion process, much research has been performed on identifying microorganisms that efficiently convert pentoses and hexoses to biofuel, such as ethanol.

While numerous microbes have been found to process hexoses into ethanol, efficiently fermenting pentoses has proven more elusive. Some bacteria and fungi can inefficiently convert pentoses to ethanol and many microbes can only process pentoses when assisted by enzymes. For a long time it was thought that yeast strains could not anaerobically ferment pentoses. However, U.S. Pat. No. 4,359,534 to Kurtzman et al. discloses the use of *Pachysolen tannophilus* to ferment pentoses. Similarly, U.S. Pat. No. 7,344,876 to Levine discloses a pure culture of *Kluyveromyces marxianus* capable of proliferation on pentoses as the sole carbon source.

While the patents to Kurtzman and Levine disclose the use of yeasts for fermentation of pentoses into ethanol, commercial applications have been limited because of the detrimental effects of inhibitory secondary products typically found in biomass hydrolysate. Yeasts that can ferment xylose and other pentoses in an artificial, or controlled, medium generally perform poorly in acid hydrolysates. Challenges presented by biomass hydrolysate include an acidic pH and a high concentration of toxic compounds, including acetic acid, phenolic compounds, 5-hydroxymethylfurfural (HMF) and furfural, and other inhibitory molecules produced during hemicellulose hydrolysis.

Because of the detrimental effects of inhibitory secondary products on the production of ethanol, biomass hydrolysate is currently subjected to a conditioning process after pretreatment and hydrolysis to reduce the concentration of inhibitory secondary products. This conditioning process adds complexity and cost to the overall process and reduces the efficiency and cost-effectiveness of the conversion process. Furthermore, the greater the required reduction in the concentration levels of the inhibitory secondary products, the greater the complexity and cost. A need, therefore, exists for a process in which microbes, such as different yeast strains, could more effectively convert pentoses, as well as hexoses, into ethanol and other biofuels in the presence of inhibitors formed during the pretreatment and hydrolysis process. In addition, it would be beneficial to develop schemes whereby inhibitory secondary products may be partially recovered and purified, instead of only removed and discarded, from hydrolysate.

Furthermore, if an efficient method for converting pentoses to ethanol existed, the discarded hemicellulose in the paper pulping process might be converted into alcohol instead. Similarly, sugar cane residues, referred to as bagasse, could also be subjected to hemicellulose conversion prior to being combusted for their fuel values. The possibility of removing hemicellulose from the paper pulping process and converting it to ethanol was hypothesized by the Georgia Institute of Technology in W. J. Fredrick et al., Co production of ethanol and cellulose fiber from Southern Pine: A technical and economic assessment, 32 Biomass and Bioenergy 1293-1302 (2008). However, the Georgia Institute of Technology process explicitly requires the hydrolysate to be conditioned to remove inhibitors and noted the lack of an efficient process to convert pentoses into ethanol. The study noted that "Fermentation is carried out after inhibiting contaminants have been removed from the hydrolysate." The study further notes that the 85% conversion factor of pentoses to ethanol "is an optimistic estimate that assumes that on-going research will make it possible . . . " The study concludes that ethanol production from loblolly pine may not be competitive with ethanol from other lignocellulosic sources when it is co-produced with cellulose fiber.

SUMMARY OF THE INVENTION

In view of the foregoing, an object according to one aspect of the present patent document is to provide an improved apparatus and process for converting biomass hydrolysate into ethanol or other biofuel. Preferably the apparatus and process address, or at least ameliorate one or more of the problems described above. To this end, a process for converting biomass hydrolysate into biofuel is provided; the process comprises the steps of: obtaining a biomass hydrolysate solution comprising monosaccharides; immobilizing a fermentative microbe contacting the solution with the immobilized fermentative microbe; and recovering a fermented biofuel. The recovered biofuel preferably comprises alcohol, and more preferably comprises ethanol.

In another embodiment, a process for converting biomass hydrolysate into biofuel is provided comprising the steps of: contacting a biomass hydrolysate solution with immobilized fermentative microbe strain for a sufficient reaction time to convert monosaccharides in the biomass hydrolysate to biofuel; and recovering biofuel from the fermented hydrolysate.

In certain implementations of the foregoing embodiments, the fermentative microbe is *Pachysolen tannophilus* and *Pachysolen tannophilus* is immobilized in calcium alginate. The calcium alginate may be in the form of beads ranging from 0.1 mm to 5 mm in diameter, and are more preferably about 2 mm to 3 mm in diameter. The calcium alginate is not required to be in bead form and may be in any other form that permits the *Pachysolen tannophilus* to be immobilized but still allows the sugar substrates in the biomass hydrolysate to kinetically interact with the yeast. For example, the calcium alginate may be in a sponge or mesh form. Similarly, the *Pachysolen tannophilus*/calcium alginate mixture may be applied as a coating to a natural or synthetic matrix to increase the surface area per mass of *Pachysolen tannophilus*/calcium alginate mixture.

Preferably, the immobilized culture of *Pachysolen tannophilus* is periodically treated with a yeast growth medium to restore metabolic efficiency to the *Pachysolen tannophilus*. The metabolic efficiency may be lost over long periods of use, especially in connection with continuous flow bioreactors.

In another embodiment, the immobilized fermentative microbe strain is at least one microbe selected from a group consisting of *Pichia*, *Candida*, *Klyveromyces* and *Zymomonas mobilis* NREL strain 8b.

In yet another embodiment, the alginate used to immobilize the culture of *Pachysolen tannophilus* is periodically recovered and recycled by treating the *Pachysolen tannophilus*/calcium alginate with a calcium chelator and monovalent counter-ion, such as sodium citrate. The resulting dialysis of the solution with an inorganic salt, such as sodium chloride, regenerates sodium alginate, from which calcium alginate may be regenerated.

In yet another embodiment, the biomass hydrolysate contains a substantial amount of secondary products that inhibit fermentation. The hydrolysate solution may contain furfural levels in the range of about 0.01 to 10 g/L, 5-hydroxymethylfurfural levels in the range of about 0.01 to 10 g/L, and acetic acid levels in the range of about 0.05 to 20 g/L, or even 0.5 to 20 g/L. In addition, the hydrolysate solution may contain phenolic compounds in the range of about 0.01 to 10 g/L. These levels of furfural, HMF, phenolic compounds, and acetic acid may occur in combination or in isolation. Other inhibitors may also be present.

In yet another embodiment, more than 80% of the monosaccharides in the solution are converted to ethanol.

In still another embodiment, the biomass hydrolysate is obtained from the biomass by pressing. The biomass and biomass hydrolysate may be subjected to a high pressure press capable of squeezing the sugar-containing liquid forming the biomass hydrolysate out of the biomass residue.

In other embodiments, the biomass hydrolysate may be conditioned by passing the hydrolysate over activated carbon, a strong acid ion exchange resin and/or a weak base ion exchange resin.

In the various embodiments described above, the biomass hydrolysate solution may contains inhibitory secondary products sufficient to prevent more than 50% conversion of pentoses by the fermentative microbes in their "free" state.

In another aspect, a process for converting biomass hydrolysate into biofuel is provided comprising the steps of: contacting the biomass hydrolysate solution with a first immobilized microbe strain; contacting the biomass hydrolysate solution with a second immobilized microbe strain; and recovering a fermented biofuel.

In one embodiment the first immobilized microbe strain is a bacterium and the second immobilized microbe strain is a yeast. Further, the first immobilized microbe strain may be contained in a first reactor and the second immobilized microbe strain may be contained in a second reactor. In an alternative embodiment, both immobilized microbe strains may be in the same reactor. If implemented so both strains are in the same reactor, the first immobilized microbe strain and the second immobilized microbe strain may also be immobilized together within the same immobilization medium.

Preferably, the immobilization medium is a calcium alginate bead, but other immobilization mediums may also be used. Further, the first immobilized microbe strain may be immobilized in a first immobilization medium and the second immobilized microbe strain may be immobilized in a second immobilization medium.

In one embodiment, the second immobilized microbe strain is capable of fermenting mannose to a biofuel.

In yet another aspect of the present patent document, a process for converting biomass hydrolysate into biofuel is provide comprising the steps of: flowing a biomass hydrolysate solution comprising monosaccharides and one or more inhibitory secondary products through a continuous flow reactor containing an immobilized microbe strain and contacting the immobilized microbe strain with the biomass hydrolysate; and recovering a fermented biofuel.

In one embodiment, the flow rate of the biomass hydrolysate is set to exceed the sedimentation rate of the immobilized microbe strain in a "free" condition. Preferably, the continuous flow reactor is an upflow reactor, but other continuous reactors may also be used.

In another embodiment, the productivity of the biofuel conversion process is at least 0.3 g/L·h for a flow rate corresponding to a 10 hour retention time. In still another embodiment, the productivity of the biofuel conversion process is at least 0.42 g/L·h for a flow rate corresponding to a 5 hour retention time.

In a further aspect, a medium for fermenting biomass hydrolysate is provided. In one embodiment, the medium comprises calcium alginate beads ranging from 0.1 mm to 5 mm in diameter, and a microbe strain capable of fermenting pentoses immobilized in the calcium alginate beads, wherein the immobilized microbe strain is capable of converting at least 70% of available pentoses in a biomass hydrolysate to a biofuel.

In yet another aspect, a medium for fermenting biomass hydrolysate is provided, comprising an immobilization substance capable of providing a micro environment for a microbe strain; and a microbe strain capable of fermenting pentoses into a biofuel immobilized in the immobilization substance, wherein the microbe strain comprises about 5% by volume of the immobilization substance.

As described more fully below, the apparatus and processes of the present patent document permit the efficient conversion of biomass hydrolysate into ethanol, even in the presence of high levels of inhibitory secondary products formed or extracted during pretreatment and/or fermentation steps of the process. Further aspects, objects, desirable features, and advantages of the methods disclosed herein will be better understood from the detailed description and drawings that follow in which various embodiments are illustrated by way of example. It is to be expressly understood, however, that the drawings are for the purpose of illustration only and are not intended as a definition of the limits of the claimed invention.

DETAILED DESCRIPTION OF THE PREFERRED EMBODIMENTS

Consistent with its ordinary meaning as a renewable energy source, the term "biomass" is used herein to refer to living and recently dead biological material including carbohydrates, proteins and/or lipids that may be converted to fuel for industrial production. By way of non-limiting example, "biomass" refers to plant matter, including, but not limited to switchgrass, sugarcane bagasse, corn stover, corn cobs, alfalfa, *Miscanthus*, poplar, and aspen, biodegradable solid waste such as dead trees and branches, yard clippings, recycled paper, recycled cardboard, and wood chips, plant or animal matter, and other biodegradable wastes.

The present patent document teaches new and improved processes and apparatuses for fermenting biomass hydrolysate. Processes used to convert polysaccharides in biomass into hexoses and pentoses often create inhibitory secondary products that prevent or hinder fermentation. Furthermore, the combinations of inhibitory secondary products found in actual biomass hydrolysate are more toxic to ferments than any single inhibitory secondary product added to a defined, artificial medium. The present patent document teaches novel processes that increase the tolerance of the fermentative microbes to inhibitory secondary products found in biomass hydrolysate by immobilizing the microbes. In certain embodiments, fermentation of hemicellulose hydrolysate containing inhibitory secondary products is carried out using immobilized *Pachysolen tannophilus*. In some embodiments, fermentation of hemicellulose hydrolysate is carried out using an immobilized microbe, even though the concentration of an individual secondary product or the combined concentration of secondary products in the biomass hydrolysate would be inhibitory to the microbe in its free state.

Immobilization confers an increased resistance on microbes to inhibitory secondary products. For example, immobilization in a calcium alginate greatly reduces the susceptibility of the yeast *Pachysolen tannophilus* to inhibitors contained in softwood hydrolysate. The benefits of immobilization, however, are not limited to *Pachysolen tannophilus*. Indeed, numerous different microbes may benefit from immobilization including, for example, yeasts from the genera *Pichia, Candida*, and *Klyveromyces*. In addition, bacterium microbes such as *Zymomonas mobilis*, NREL strain 8b, also show an increased resistance to inhibitory secondary products when immobilized.

Preferably the calcium alginate, or other material used to immobilize the microbes, is in a form with a high surface area such as in bead, sponge, or mesh form. In addition, the immobilized microbe or combination of microbes should also be able to ferment monosaccharides found in hemicellulose hydrolysates—including the hexoses mannose, galactose and glucose and the pentoses xylose and arabinose—to biofuel with high efficiency.

Figure 1:
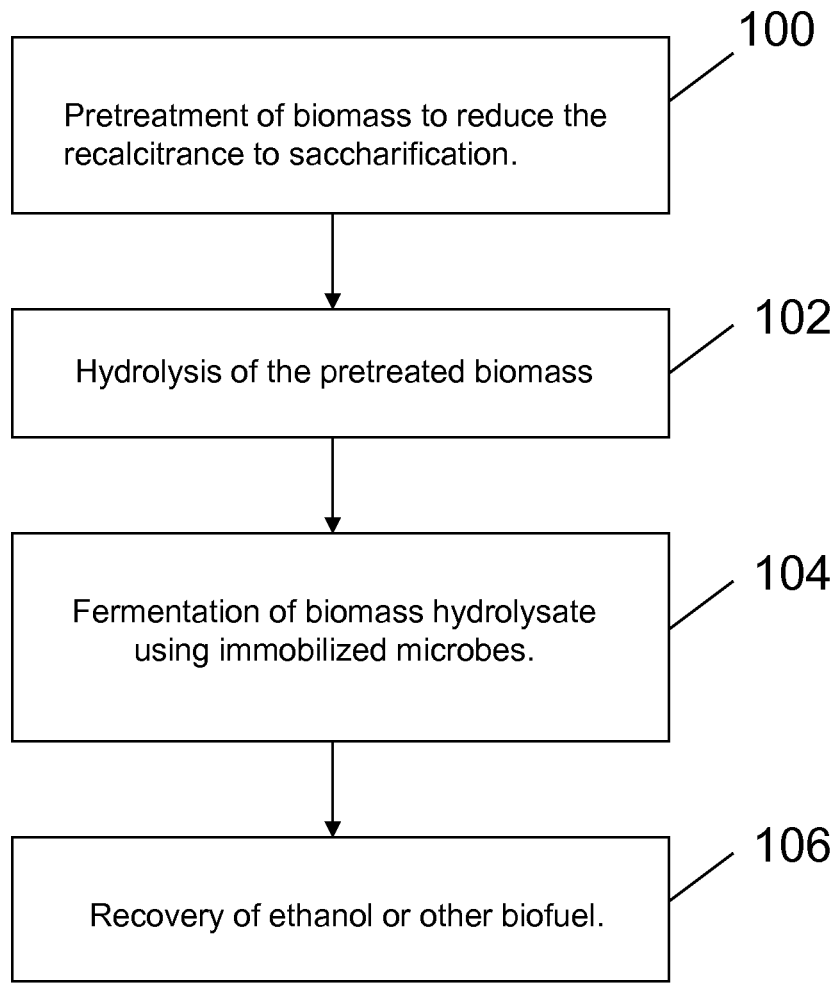
FIG. 1 illustrates an overview of one embodiment of a process for the conversion of biomass into a biofuel such as ethanol.
Figure 2:
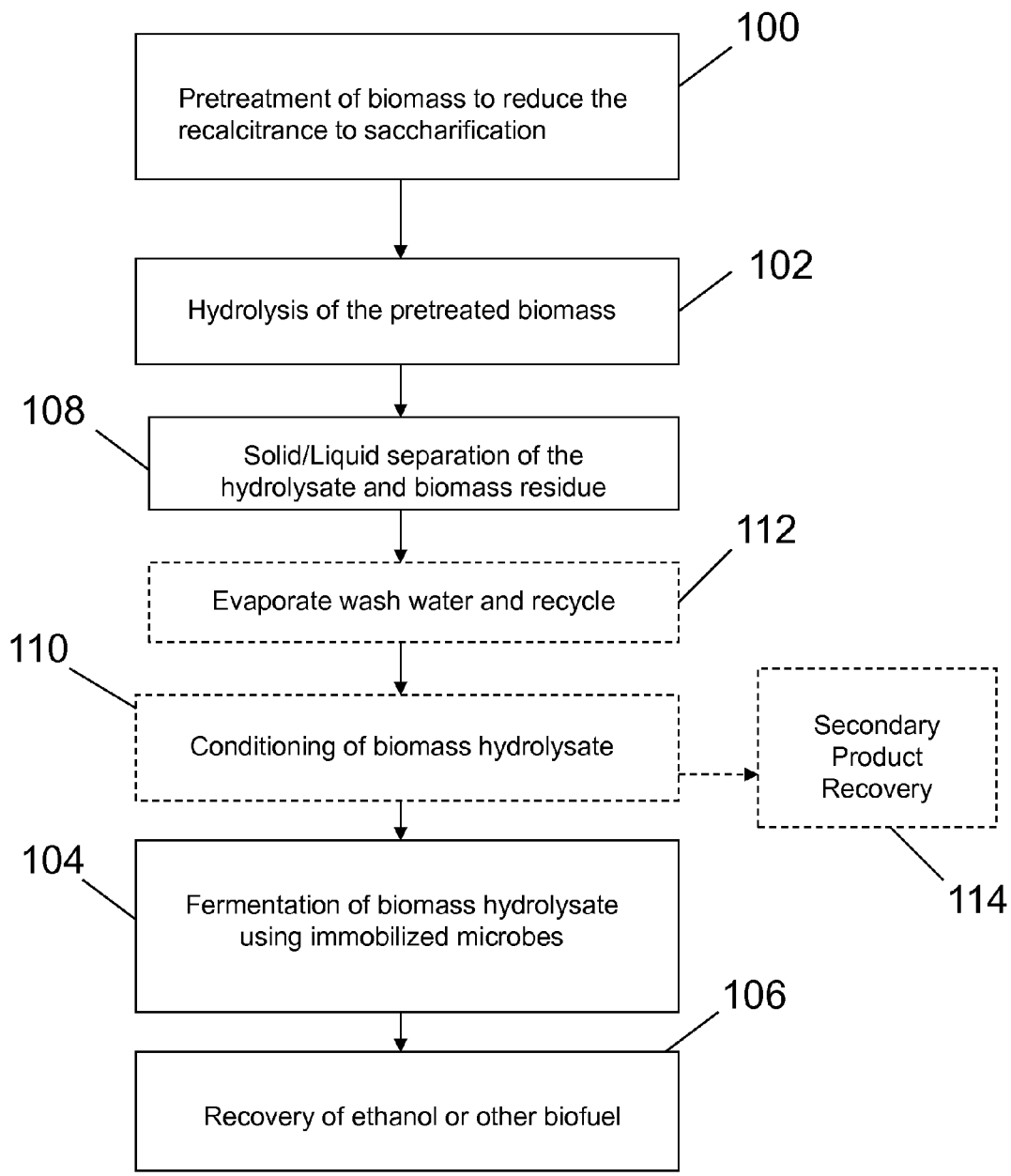
FIG. 2 illustrates an overview of another embodiment of a process for the conversion of biomass into biofuels such as ethanol.

FIG. 1 illustrates a general overview of one embodiment of a process for converting biomass to ethanol or other biofuels. The primary steps include pretreatment 100, hydrolysis 102, fermentation 104, and biofuel recovery 106. FIG. 2 illustrates another embodiment of a process for converting biomass to ethanol or other biofuels. The process in FIG. 2 differs from that in FIG. 1 in that it also includes a solid/liquid separation step 108, an optional evaporation step 112, an optional conditioning step 110, and an optional secondary product recovery step 114. If the biomass hydrolysate is provided from another source instead of generated on site, the process of the present patent document may be condensed to performing step 104 or steps 104 in combination with step 106.

Before biomass can be fermented, it often needs to undergo some form of process to disrupt the polymer network of cellulose, hemicellulose, and lignin forming the biomass structure so the polysaccharides can be reduced to monosaccharides. This process is commonly referred to as "pretreatment" and is designed to reduce the recalcitrance of the biomass to enzymatic or chemical saccharification of the cellulose and hemicellulose, therein. The pretreatment step 100 may occur through a number of methods, including for example, in a pressure reactor. Table 1 lists appropriate ranges for temperature, dwell time, and moisture content suitable for pretreatment in a pressure reactor. However, other operating conditions may also be suitable.

TABLE 1

Pressure Reactor Pretreatment Conditions

| | |
|---|---|
| Temperature* | 105-200° C. |
| Time | 1 minute-24 hours |
| Moisture Content | 25-95% |

*Temperature dictates the pressure in a sealed vessel assuming a saturated steam system Effectiveness of the pretreatment step 100 may be increased by adding one or more reagents. Reagents may include, but are not limited to: nitric acid, phosphoric acid, hydrochloric acid, sulphuric acid, sulphur dioxide, and sodium sulphite. Other reagents that reduce the recalcitrance of the biomass to hemicellulose removal may also be added.

In addition to performing pretreatment 100 in a pressure reactor, pretreatment 100 may be performed using a number of other methods, including acid prehydrolysis, steam cooking, alkaline processing, rotating augers, steam explosion, ball milling, or any other method that reduces the recalcitrance of the biomass to saccharification of the cellulose and hemicellulose contained therein.

Once the cellulose and hemicellulose are exposed through pretreatment 100, the polysaccharides are broken down into their monosaccharide components so they can be fermented. The Hydrolysis step 102 is used for converting the polysaccharides into fermentable sugars. In some of the harsher pretreatments 100, hydrolysis 102 may occur simultaneously with the pretreatment step 100 and a separate hydrolysis step 102 is not required. The two basic forms of hydrolysis 102 are thermo-chemical and enzymatic. Thermo-chemical hydrolysis is typically performed using a concentrated acid such as sulfuric acid or hydrochloric acid at relatively low temperatures or by using a dilute acid at relatively high temperatures.

Once the monosaccharides have been generated through the hydrolysis step 102, fermentation can begin. Although fermentation can occur within the biomass residue with some fermentation techniques, in the processes described in the present patent document, a biomass hydrolysate solution comprising monosaccharides will typically be obtained by pressing and/or washing the biomass residue. The obtained biomass hydrolysate is then fermented ex-situ in fermentation step 104.

Recovery of the sugars from the biomass residue is preferably achieved through solid-liquid separation. For example, as shown in FIG. 2, a solid-liquid separation step 108 may be used to recover the sugars from the biomass residue. Solid-liquid separation may be performed using a number of methods including, but not limited to, centrifuging or pressing. Preferably, pressing may be accomplished with a hydraulic press. However, numerous types of mechanical or machine presses may be used. For example, a mechanical press such as a conventional screw press, a hydro-mechanical press, a pneumatic press or any other type of press that can apply the necessary pressure to remove the hemicellulose hydrolysate from the cellulose/lignin residue may be used. The press may have a range of capabilities and configurations for pressing out the hemicellulose hydrolysate. Preferably the press can generate from at least about 10.5 kg/cm$^2$ to about 21.1 kg/cm$^2$. In other embodiments, it is desirable if the press can generate at least approximately 1,410 kg/cm$^2$.

Pressing has additional advantages because the biomass residue (which will comprise cellulose and lignin at this point) may be more valuable as a coal replacement if its density can be maximized and its moisture content minimized, thereby increasing its energy density. For pulp mill feed there are no requirements for moisture or density but minimization of fiber damage is important. Pulp quality is measured based on its fiber length, among other variables, but not moisture content. However, if a high energy density fuel replacement is made instead of paper pulp, reducing the moisture content is an important factor.

Accordingly, the final product that the biomass residue is to eventually be used for may determine what size and kind of press to use for solid/liquid separation. For example, if the biomass residue is to eventually be used to generate cellulose and/or lignin fibers to make paper products, cardboard, or fiberboard, a lower pressure, such as in the range of 10.5 kg/cm$^2$ to 21.1 kg/cm$^2$ may be advantageous to minimize damage to the cellulose fibers. In processes that turn the biomass residue into high energy density fuel, higher pressures may be used to minimize the moisture content, without regard to fiber quality. As a result, it may be desirable to employ pressures of about 1,410 kg/cm$^2$ or even higher. In other embodiments, however, pressures within the range of 10.5 kg/cm$^2$ to 21.1 kg/cm$^2$ may still be used, as presses generating these types of pressures are readily available and comparatively inexpensive as compared to presses that are capable generating about 1410 kg/cm$^2$ of pressure. For example, presses that generate between about 10.5 kg/cm$^2$ and 21.1 kg/cm$^2$ of pressure are routinely used in the wine and olive oil industries to press grapes and olives, respectively.

When sugarcane bagasse is used as the biomass from which the hydrolysate is pressed, fiber condition is generally unimportant. However, when used as a high energy density fuel replacement, the moisture content is an important factor. Therefore, higher, rather than lower pressures, may be desirable for purposes of performing the solid/liquid separation step 108.

Pressing is also advantageous because it reduces dilution from wash water. Using wash water to separate the hydrolysate from the biomass will dilute the sugar stream and thus lower the resulting ethanol concentration in the fermented hydrolysate. If wash water is used, however, dilution of the sugar stream may be mitigated by the use of evaporators or similar machinery to reduce water content in the hydrolysate through optional evaporation step 112, shown in FIG. 2. The recovered water from evaporation may be recycled into subsequent wash processes. Addition of an evaporation step 112 as a process step increases the sugar concentration of the hydrolysate and thus the ethanol concentration resulting from fermentation, which in turn reduces the costs of distillation.

Once the monosaccharides are separated from the biomass, there are a number of microbes that may be used for converting the monosaccharides of the biomass hydrolysate into ethanol or other biofuels in fermentation step 104. For example, if the biomass hydrolysate comprises a cellulose hydrolysate, so as to include glucose (which is a hexose), the glucose in the hydrolysate may be fermented by a number of yeast strains including *Saccharomyces cerevisiae* (traditional baker's yeast) and *Kluyveromyces marxianus* to name a few.

On the other hand, if the biomass hydrolysate comprises a hemicellulose hydrolysate, the hydrolysate will include the pentoses xylose and arabinose, and a lower concentration of hexoses, except in the case of softwood hydrolysate. In the case of softwood hemicellulose, the hexose mannose is the major saccharide and the pentose xylose is the next most abundant. Microbes that can convert the combination of pentoses and hexoses found in hemicellulose hydrolysate into ethanol are not as abundant as those available for cellulose hydrolysate. To convert sugars from hemicellulose hydrolysate into ethanol, microbes that can convert both five-carbon and six-carbon sugars are preferably utilized so that all of the available constituent sugars of the hemicellulose hydrolysate may be converted to ethanol or other biofuels. The same is true if the biomass hydrolysate comprises a combination of cellulose hydrolysate and hemicellulose hydrolysate. Microbes that can ferment hexoses and pentoses may be derived from the genera *Pachysolen, Kluyveromyces, Pichia*, and *Candida. Pachysolen tannophilus* is preferably used in fermentation of a liquid hydrolysate comprising a hemicellulose hydrolysate. In particular, when immobilized, *Pachysolen tannophilus* has been found to effectively ferment hemicellulose hydrolysate produced from softwood.

In addition to immobilized yeasts, immobilized bacterium may also be used to ferment hexose and pentose sugars in biomass hydrolysate. For example, the recombinant bacterium *Zymomonas mobilis* (NREL recombinant 8b) may be used to ferment hemicellulose hydrolysate produced from softwood, hardwood, and/or herbaceous sources.

Microbes with complementary metabolic properties may also be combined in the same fermentation process in step 104 to allow their complementary properties and abilities, such as complementary hexose and pentose fermentation capabilities or complimentary metabolic rates, to be used together. For example, recombinant *Zymomonas* is unable to ferment mannose, the most prevalent sugar contained in softwood hydrolysate, the recombinant *Zymomonas mobilis* is preferably paired with a complementary yeast or bacterium that is able to effectively ferment the hexose mannose to ethanol or another biofuel when it used to ferment softwood hydrolysate. On the other hand, in the case of sugarcane bagasse, where the hydrolysate primarily comprises xylose and glucose, another microbe is not required to assist the recombinant *Zymomonas* to achieve a satisfactory fermentation of the contained sugars.

Other combinations of microbes are also possible including pairing different bacterium together, pairing different yeasts together, pairing various yeasts and bacterium together, or pairing or combining any number of microbes with complimentary features including using any number of microbes at the same time. As the number of combined microbes increases, however, their capabilities may begin to overlap significantly and thereby reduce the additive value of the additional microbes.

Depending on the biomass and treatments employed, the pretreatment step 100 and hydrolysis step 102 may yield soluble sugars from the biomass in the form of xylose, mannose, arabinose, galactose, and glucose ready for fermentation in step 104. However, other secondary products, which are inhibitory to the fermentation step 104, are also produced or extracted from the biomass. The concentrations of fermentation inhibitors that form in converting biomass to fermentable hexoses and pentoses will vary depending on the source of the biomass and the methods used for the pretreatment step 100 and the hydrolysis step 102. For example acetic acid is produced by cleavage of acetyl groups from hemicellulose. In addition, some of the pentoses and hexoses are degraded due to dehydration into furfural and HMF. Phenolic and polyphenolic compounds (collectively "Phenolic Compounds") are also formed from the degradation of lignin. While the generated Phenolic Compounds, furfural, HMF, and acetic acid are all potentially valuable compounds, they are also fermentation inhibitors, and may prevent or inhibit fermentation, particularly as their concentrations increase.

In addition, Furfural and HMF degrades to produce levulinic acid, acetic acid, and formic acid, which are even more potent fermentation inhibitors. Phenolic and polyphenolic compounds produced from hydrolysis of wood hemicellulose and the concomitant lignin degradation include guaiacol, vanillin, phenol, vanillic acid, syringic acid, salicylic acid, gentisic acid, and others. Many of these compounds, for instance vanillin and vanillic acid, are known to inhibit the growth of and/or fermentation with microbial yeasts, such as *Pachysolen* and *Saccharomyces*.

In addition to secondary products made from the degradation of hemicellulose components, other molecules may be extracted from biomass by the pretreatment and/or saccharification conditions during the pretreatment step 100 and/or hydrolysis step 102. These extracted compounds may include terpenes, sterols, fatty acids, and resin acids. These extracted compounds can also be inhibitory to metabolic processes, including fermentation, in yeast and other microbes, such as bacteria.

Furthermore, metal cations including calcium, aluminum, potassium, and sodium are found in hemicellulose hydrolysate and heavy metals may be present from degradation of the metal vessels due to hydrolysis. The presence of such metal cations may also be inhibitory above certain concentrations.

As made clear from the foregoing discussion, the environment experienced by microbes in biomass hydrolysate is in stark contrast to a defined, artificial medium where all or most of these additional inhibitors are not present or are added experimentally one at a time to study their effects. Indeed, in a biomass hydrolysate the various inhibitory compounds discussed above, as well as others, may work synergistically with one another so that a non-inhibitory amount of a certain compound may become inhibitory in the presence of one or more additional compounds that are also below their respective individual inhibitory concentrations.

Because many secondary products can degrade the fermentation process as their concentrations increase, prior methods for conversion of biomass into ethanol have employed a costly conditioning step to remove or reduce the concentration of inhibitors from the hydrolysate prior to fermentation. Furfural, HMF, and acetic acid, as well as phenolics are the most commonly found inhibitors in biomass hydrolysate. Levels in the range of 0.2-5.0 g/L furfural, 0.2-6.0 g/L HMF, and 3.0-10.9 g/L acetic acid are considered common and may greatly reduce fermentation or prevent it all together. Likewise, concentrations of phenolics in the range of 0.1-10 g/L are common and may be inhibitory. A method commonly used to ameliorate the toxicity of hydrolysates by reducing HMF and furfural concentration is pH adjustment through "overliming" with calcium hydroxide. Overliming is the process whereby lime is added beyond that necessary for pH adjustment. Even after overliming, however, high levels of inhibitors may still exist. In addition, overliming precludes recovery of secondary products that have high value from the hydrolysate.

In order to deal with the potential for high levels of inhibitory secondary products often found in biomass hydrolysate—for example, levels that would inhibit the fermentation microbes in their free state—during the fermentation step 104, the present patent document teaches processes to protect the fermentation microbes from the degradation effects of the inhibitors by immobilizing the microbes, and more preferably immobilizing the microbes in calcium alginate. Immobilization of microbes is the attachment or inclusion in a distinct solid phase, such as calcium alginate, that permits exchange of substrates, products, inhibitors, etc. with the microbe, but at the same time separates the microbes from the bulk biomass hydrolysate environment. Therefore, the microenvironment surrounding the immobilized microbes is not necessarily the same as that which would be experienced by their free-cell counterparts. As a result, for example, the present patent document teaches processes for immobilizing *Pachysolen tannophilus* and for fermenting pentoses and hexoses in the presence of inhibitors found in hemicellulose hydrolysate, even at concentrations that would inhibit the fermentative microbe in its free state.

By immobilizing the fermentative microbe(s) during the fermentation step 104, the need for conditioning the biomass hydrolysate to reduce the concentration of, or possibly even completely remove, inhibitory secondary products is significantly ameliorated. This is because the need to lower the concentration of inhibitory secondary products to the levels necessary for fermentation using free microbes is eliminated. Thus, as reflected in FIG. 1, conditioning to reduce the concentration of inhibitors may be omitted in some embodiments, or, as shown in FIG. 2, included as an optional conditioning step 110.

Conditioning the biomass hydrolysate in conditioning step 110 to reduce the concentration of inhibitory secondary products may still be desirable where, for example, the concentration of the secondary products (either individually or in combination) is sufficiently high to interfere with the fermentation of sugars even by the immobilized microbe(s). In such cases, however, the concentration of the inhibitory secondary products will generally not need to be reduced to the same levels as necessary for fermentation using free microbes and thus a less severe and less costly conditioning process may be employed. To offset the costs associated with the overall fermentation process, it may also be desirable to recover secondary products having a high value through an optional high value secondary product recovery step 114 shown in FIG. 2. Following partial removal (and possible recovery) of many secondary products from the biomass hydrolysate, however, the concentrations of these products may remain sufficiently elevated within the hydrolysate, particularly considering the synergistic nature of the inhibitors, to interfere with fermentation of sugars to ethanol or other biofuel by the fermentative microbe(s) in their free state. Accordingly, the use of immobilized fermentative microbe(s) in fermentation step 104 is an important aspect of the processes described herein, even when the optional conditioning step 110 is employed to reduce the concentration of secondary products contained in the biomass hydrolysate.

In some instances, it may also be desirable to perform conditioning step 110 even when the concentration of inhibitory secondary products is insufficient to inhibit fermentation by the immobilized microbe(s) where, for example, the secondary products have high value and thus it is desirable to separately recover the high value secondary products through high value secondary product recovery step 114. This may be desirable, for example, where the net value of the recovered high value secondary products may be used to offset, and hence lower, the costs associated with the overall fermentation process.

There are numerous methods of performing the conditioning step 110 to reduce the concentrations of inhibitory secondary products. Employing different conditioning methods for conditioning step 110 will result in different concentration levels of inhibitory secondary products remaining in the hydrolysate. The method of conditioning chosen for conditioning step 110 may depend on a variety of factors, including the sensitivity of the microbe used during fermentation to inhibitory secondary products, costs, and whether there is a desire to recover high value secondary products during a recovery step 114. The more sensitive the microbe, the more desirable it will be to reduce the concentration of the inhibitory products from the biomass hydrolysate during conditioning of the hydrolysate in step 110. Immobilization of the fermentative microbe(s), however, will decrease the sensitivity of the microbe to inhibitory secondary products and thus may reduce the complexity and costs incurred during conditioning step 110. Some of the conditioning methods that may be employed in conditioning step 110 to reduce the concentration of secondary products include, but are not limited to: 1) overliming of hydrolysate; 2) activated carbon (AC) treatment followed by pH adjustment; 3) ion exchange followed by overliming; 4) AC treatment followed by ion exchange; and 5) AC treatment followed by nanofiltration.

When hydrolysate from solid-liquid separation step 108 contains one or more high value secondary products, the secondary products may be recovered in step 114 from the hydrolysate and subsequently used for other purposes. Some of the high-value secondary products that may be recovered in step 114 include, but are not limited to, the mineral acid used in the pretreatment process 100, such as sulfuric acid, acetic acid hydrolyzed from hemicellulose polymers, antioxidant molecules (phenolic and polyphenolic compounds) liberated from the partial hydrolysis of lignin during hydrolysis step 102, other organic acids, nutraceutical, cosmeceutical, or pharmaceutical products, and different furans and furan derivatives, such as 5-hydroxymethylfurfural and furfural. High value secondary product recovery step 114 may be accomplished by adsorption of the secondary products to different matrices, including activated carbon, ion exchange resin, ion exchange membrane, organic molecule "scavenging" resins, polystyrene beads, or any other similar type medium with a high surface area. High value secondary product recovery step 114 may also be accomplished by separating the secondary product(s) from the soluble hexoses and pentoses through ion exclusion chromatography, pseudo-moving bed chromatography, high performance liquid chromatography or by filtration methods including micro-, nano-, and ultrafiltration using hollow fiber or membrane technologies. High value secondary product recovery step 114 may include several of the aforementioned processes in series to recover different molecular species. Furthermore, the recovery process(es) employed in step 114 may be tailored to recover specific secondary products according to the nature of the starting biomass. Because many of the recovered secondary products (acetic acid, furans and their derivatives, phenolic and polyphenolic compounds, levulinic acid, formic acid, and others) are inhibitory to yeast and bacterial fermentation of sugars to ethanol, recovery of high value secondary products in step 114 may both increase the economics of the entire process and allow for more efficient fermentation in step 104 of the pentoses and hexoses.

In general, microbes may be immobilized for fermentation 104 of biomass hydrolysate in step 104 using a number of different methods. Microbes may be bound to a matrix material or, more preferably, immobilized by entrapment in the matrix material. For example, microbes may be immobilized by entrapment using a drop-forming procedure. The resultant beads may be of different size and possess different pore sizes. For example, the beads may range in size from 0.1 mm to 5 mm in diameter, more preferably the beads may range from 2 mm to 3 mm in diameter, and more preferably the beads are about 3 mm in diameter.

The drop-forming procedure may be enhanced through a number of processes. The beads, may be hardened to different degrees and may have coatings applied to withstand shear forces in a reactor and to reduce cell loss. For example, if calcium alginate is used, the beads may be dried to increase compression stress. The beads may also be hardened by glutaraldehyde treatment or coated with catalyst-free polymer to enhance their stability. The beads may be recoated with plain alginate as a double layer to enhance their gel stability. Furthermore, the beads may have a polyacrylamide coating to enhance their structural stability. The beads may also be coated with a copolymer acrylic resin to increase diffusion and reduce cell leakage. Similarly, other additions to the drop forming procedure may be incorporated to enhance the effectiveness of the matrix.

Other techniques for improving the efficiency of immobilized microbes include increasing the surface area of the microbe/immobilization medium mixture once it is formed. For example, a *Pachysolen tannophilus*/calcium alginate or other microbe/calcium alginate mixture may be applied as a coating to a natural or synthetic, high surface area, support structure. In one implementation, the support structure only need be able to support the microbe/immobilization medium and itself. For example, the support structure may comprise a ceramic sponge, honeycomb, reactor packing material or other support structure to increase the surface area per mass of the microbe/immobilization medium when it is applied. The mixture may also, or in the alternative, be applied to parts of the reactor surfaces, such as, the walls or the surface of the mixing devices.

In addition to immobilization by entrapment, the microbes may be immobilized by other methods including adsorption, cross-linking, or immobilized by any other means capable of providing a micro-environment for the microbe.

A variety of different materials may be used to immobilize microbes. If the microbes are immobilized using entrapment calcium alginate, a natural product from brown algae (seaweed) may be preferably used. However, other materials, both natural and synthetic, may also be used to immobilize microbes using entrapment including carrageenan, xanthan gums, agarose, agar and luffa, cellulose and its derivatives, collagen, gelatin, epoxy resin, photo cross-linkable resins, polyacrylamide, polyester, polystyrene and polyurethane.

Other materials that may be used to immobilize microbes using adsorption or other immobilization methods include kieselguhr, wood, glass ceramic, plastic materials, polyvinyl acetate, and glass wool.

When combining microbes with complimentary properties, the microbes may be combined within the same immobilization vehicle, or the microbes may be immobilized separately and the separately immobilized microbes combined in the same fermentation reactor. For example, if calcium alginate beads are used as the immobilization vehicle, different complimentary microbes may be combined within the same bead. As one example, to effectively ferment softwood hydrolysate, which contains the sugars mannose, galactose, glucose and xylose, to ethanol, one may combine *Zymomonas mobilis*, NREL strain 8b, which ferments glucose and xylose to ethanol, with *Saccharomyces cerevisiae*, which ferments mannose and galactose, into a single bead product. In this way advantageous fermentative properties of different microbial species are combined in a single bead product.

Alternatively, separate beads can be made containing each microbe and then the beads may be combined in the fermentation reactor. For example, the fermentation of the hexoses and pentoses to fuel may be performed by combining beads composed of different microbial species with complementary hexose and pentose specificities, metabolic rates, or the like. In yet another example, different microbes are immobilized in separate reactors and the biomass hydrolysate is then run through each reactor to expose the biomass hydrolysate to each microbe. In addition, different immobilization methods may be combined with different microbes.

One of the many advantages of immobilizing the microbes is that the microbes become more stable and bioreactors may be run in a continuous mode instead of batch mode. Running the bioreactor in a continuous mode is advantageous for efficiency reasons but the microbes may begin to lose metabolic efficiencies after long periods of use. In order to restore metabolic efficiency, immobilized microbes may be periodically treated with yeast growth medium. For example, *Pachysolen tannophilus* and other fermentative microbes immobilized in calcium alginate may be periodically treated with a yeast growth medium to restore metabolic efficiency.

Another advantage of microbe immobilization is that the microbe biomass may be better retained within a continuous fermentation reactor. In a continuous fermentation process involving a high flow rate, such as that which may be experienced during the continuous running of a columnar up-flow reactor, free cells will tend to wash out. Wash out reduces the number of cells in the reactor and thus lowers the rate of the fermentation reaction. To maintain the rate of fermentation, new cells must be propagated and added to the reactor, increasing costs. The examples associated with Table 2 below demonstrate the advantages of using immobilized microbes in a continuous fermentation process under wash out conditions (i.e., under a flow rate that would cause wash out of more than 5% of the free cells.)

TABLE 2

Effect of cell washout on ethanol concentration and productivity in a continuous reactor.

| Retention time (h) | Cells | Ethanol (g/L) | Productivity (g/L · h) |
|---|---|---|---|
| 10 | Imm | 3.03 | 0.30 |
|  | Free | 1.84 | 0.18 |
| 5 | Imm | 2.08 | 0.42 |
|  | Free | 0.68 | 0.14 |

Imm—immobilized

The data in Table 2 illustrates the benefits of immobilization to prevent wash out for one particular fermentative microbe. Specifically, the example in Table 2 demonstrates the improvement of biofuel (e.g., ethanol) yield for immobilized *Pachysolen tannophilus* (NRRL Y2460) over free cells of the same microbe during continuous fermentation in a column up-flow reactor. However, immobilization can be used to prevent wash out for any type of fermentative microbe in any continuous flow bioreactor and thereby increase ethanol or other biofuel yield.

The data presented in Table 2 was generated by adding $8.38 \times 10^{11}$ cells of *Pachysolen tannophilus* to two identical up-flow reactors. In the first reactor, the cells were immobilized in 2-3 mm calcium alginate beads. In the second reactor, the cells were added free in solution. Both reactors, were connected to the same reservoir of artificial medium and the same peristaltic pump was used to pump the artificial medium through the reactors during the continuous fermentation process. The artificial medium within the reservoir contained 10 g/L yeast extract, 20 g/L peptone, 7.2 g/L glucose, and 42.5 g/L xylose. The artificial medium was pumped into the bottom of both reactors simultaneously at the same rate and both reactors were incubated at 30° C.

In a first test, the two reactors were each run at a flow rate corresponding to a retention time of 10 hours. The reactors were each run for a total of 20 hours or for a total of 2× the retention time. In a second test, set up as indicated above, the two reactors were each run at a flow rate corresponding to a retention time of 5 hours. In the second test, the reactors were run for a total of 10 hours, or again for a total of 2× the retention time. The ethanol content of the first and second reactor's effluent was analyzed for ethanol content at the end of the 2× retention time period for each test. Hence, ethanol content of effluent was determined for each reactor at two separate flow conditions. The productivity (ethanol production per hour) was also determined for each flow condition. The results are reported in Table 2.

Table 2 reveals that the ethanol concentration at the end of 20 hours for the 10 hour retention time flow rate was much greater for the reactors containing immobilized *Pachysolen* than free *Pachysolen*, 3.03 versus 1.84 g/L, respectively. The corresponding productivity was also greater for the immobilized *Pachysolen*. For the second test, which employed a flow rate that resulted in a 5 hour retention time, the ethanol concentration in the effluent of the reactor containing immobilized cells was 2.08 g/L at the end of 10 hours or 2× the retention time, but the productivity increased by 40% over that in the first test due to the faster flow rate.

In contrast, at the flow rate that resulted in a 5 hour retention time, the ethanol concentration in the reactor containing free cells decreased from 1.84 to 0.68 g/L and the productivity experienced a 23% decrease, from 0.18 to 0.14 g/L*hour.

The examples of Table 2 illustrate that immobilizing fermentative microbes decreases wash out and increases biofuel, such as ethanol, productivity in the reactor. When the cells were not immobilized, the flow rate of the medium exceeded the sedimentation rate of the free *Pachysolen tannophilus* (at both flow rates tested) and the concentration of the cells in the free state reactor decreased to a low level causing the ethanol concentration and ethanol productivity to also decrease. By contrast, the *Pachysolen tannophilus* that was immobilized in the calcium alginate beads remained in the reactor and the reactor was able to increase the ethanol productivity with the increased flow rate.

Certain microbes that can be used in conversion of sugars to biofuels are motile; that is, they possess cilia and/or flagella and swim in fermentation medium. Another advantage of immobilization is that the motile microbe biomass may be better retained within a continuous fermentation reactor, even in fermentation process involving a low flow rate. Motile cells in the free state will tend to wash out in all flow conditions. Wash out reduces the number of cells in the reactor and thus lowers the rate of the fermentation reaction. To maintain the rate of fermentation, new cells must be propagated and added to the reactor, increasing costs.

Another advantage of immobilizing microbes is the ability to obtain a high biomass concentration in a continuous fermentation process. In a column upflow reactor, as a non-limiting example, more than half, preferably about two thirds to about three quarters of the reactor volume will be composed of the bead material and the rest will be inter particle void volume when the fermentative microbes are immobilized in beads of about 2 mm to 3 mm in diameter. In the case of using yeast as the fermenting microbe, where 5% of the volume of the bead is yeast biomass, the reactor will effectively contains about 3.3 to 3.75% by volume yeast biomass, which is a relatively high yeast concentration for a fermentor.

Other benefits of yeast and bacteria immobilization by entrapment in calcium alginate over free cells in suspension include greater ethanol tolerance, possibly due to changes in cell membrane composition; greater specific ethanol production, increased rate of ethanol production due to increased glucose uptake and lower dissolved $CO_2$ in solution, and increased thermo-stability of bacteria.

As described above, there are numerous methods of actually immobilizing the microbes. In one preferred embodiment for immobilizing *Pachysolen tannophilus* in calcium alginate, the microbes are initially immobilized in sodium alginate which is then converted to calcium alginate. Sodium alginate can have different viscosities when a given amount is dissolved in an aqueous solution. Viscosities for different sodium alginate products range from 100 or 200 mPa, to even as much as 1236 mPa. In a preferred embodiment, alginate with medium-low viscosity of about 324 mPa is used to produce beads, although alginates with different viscosities may be used for different biomass hydrolysates or for solid-state ferments.

The sodium alginate is prepared by adding from 0.05 to 10%, or preferably about 3.5% (w/v) sodium alginate to deionized water. Alternatively, the sodium alginate can be dissolved into growth medium, into a mixture of vitamins, including biotin, or into growth medium supplemented with vitamins, or into a natural solution containing biotin. The initial sodium alginate concentration will depend on the final concentration desired to produce beads and on the volume added by mixing with a concentrated microbe slurry.

In order to get some sodium alginate preparations into solution, the mixture may be heated and stirred on a stir plate. However, heating alginate polymers may cause some amount of hydrolysis of the alginate and thereby change the properties of the alginate solution, including its viscosity. As a result, it may be desirable to use a sodium alginate preparation that does not require heating in order to go into solution. In embodiments where the alginate may not be heated for solubilization nor autoclaved for sterilization, it may be desirable to treat the alginate with a chemical sterilizer or it may be desirable to irradiate the alginate with ultraviolet light for sterilization.

Cells may be cultivated in their respective media, and pelleted by centrifugation. Alternatively, a mass of *Pachysolen* or other in fermentative microbe may be propagated in at least a 10 L, or more preferably at least a 200 L, or even more preferably at least a 2000 L bioreactor to a concentration of about 1 to about 20 grams wet mass per liter growth medium. The resulting biomass may then be concentrated using, for example, a tangential flow filtration device to produce a 20-70% wet mass slurry of *Pachysolen* cells. This technique is particularly well suited for the production of large volumes of calcium alginate beads having one or fermentative microbes, such as *Pachysolen*, immobilized therein.

Following concentration, the concentrated cells are then recovered and thoroughly mixed with the sodium alginate medium. Mixing the alginate with the microbial cells can occur in the same device as is used for the resuspension of the alginate or in a separate device. The mixing continues to homogenity of the mixture. Mixing of the microbes with the highly viscous sodium alginate solution requires a mixing method that does not shear the microbes, such as a reciprocating disc mixer. The cell loading into the sodium alginate medium is both organism and substrate dependent. For example, a suitable target loading for *Pachysolen tannophilus* in hydrolysate is at least 5 g cells/100 mL sodium alginate medium.

Calcium alginate beads are produced by extruding the sodium alginate medium/cells into a sterile calcium chloride solution. A peristaltic pump and sterilized Master-flex Bulk-Packed Silicone Tubing that has an attached sterile 18 G needle may be used in the extruding process. The entire process is preferably done aseptically. In an alternative embodiment that is more suitable where large amounts of immobilized microbe beads are desired to be produced, a sterile 96 hollow 19 gauge pin device may be used in place of an 18 gauge needle. The beads may then be produced by extrusion and gravity dropping. Other methods may include a so-called Jet Cutter to produce beads from a continuous stream of an alginate/microbe slurry. Other modifications of producing beads from a continuous stream include using electrostatic attraction to produce droplets, using vibration to produce droplets, using air to produce droplets, and using a rotating disk atomizer, to name a few.

In order to exchange sodium ions with calcium ions to effect polymerization of the alginate, beads are dropped in a solution containing calcium chloride. In one method, a 0.22M solution of calcium chloride dihydrate is also prepared in deionized water to receive sodium alginate/microbe mixture. The sodium alginate medium and calcium chloride solution may both be autoclaved for sterilization purposes. The beads may be kept at 4° C. in the calcium chloride solution for about 60 minutes to harden. Once the beads have hardened, they are preferably rinsed several times with sterile deionized water. In a preferred embodiment, the beads are dropped into sterile growth medium containing 0.1 to 0.25 M calcium chloride. The growth medium may also contain different vitamins or biotin. After about 30 minutes of hardening, the beads may be either used immediately in a fermentation or may be stored at 4° C. until use. There is no need to rinse beads prior to use or prior to storage when hardening is carried out in such a growth medium.

In certain implementations, it may also be desirable to recycle components of the immobilization processes. The solid calcium alginate used to immobilize microbes in beads or on a support structure may delaminate, break-up, shear, or otherwise physically degrade after prolonged use. In addition, the microbe/calcium alginate mixture may also become degraded and discolored through repeated use due to the trapping of contaminants such as extractives, microbial inhibitors, and other materials. Degradation of the structure, whether due to physical and/or chemical degradation affects the performance of the fermentation process. To overcome deleterious effects of this degradation, new or fresh microbe/calcium alginate mixture may be used in the bioreactor to improve the reactors performance. However, the frequent replacement of the mixture may be uneconomical both in terms of the material costs associated with production of the calcium alginate, but also due to the cost of the lost microbes.

Figure 3:
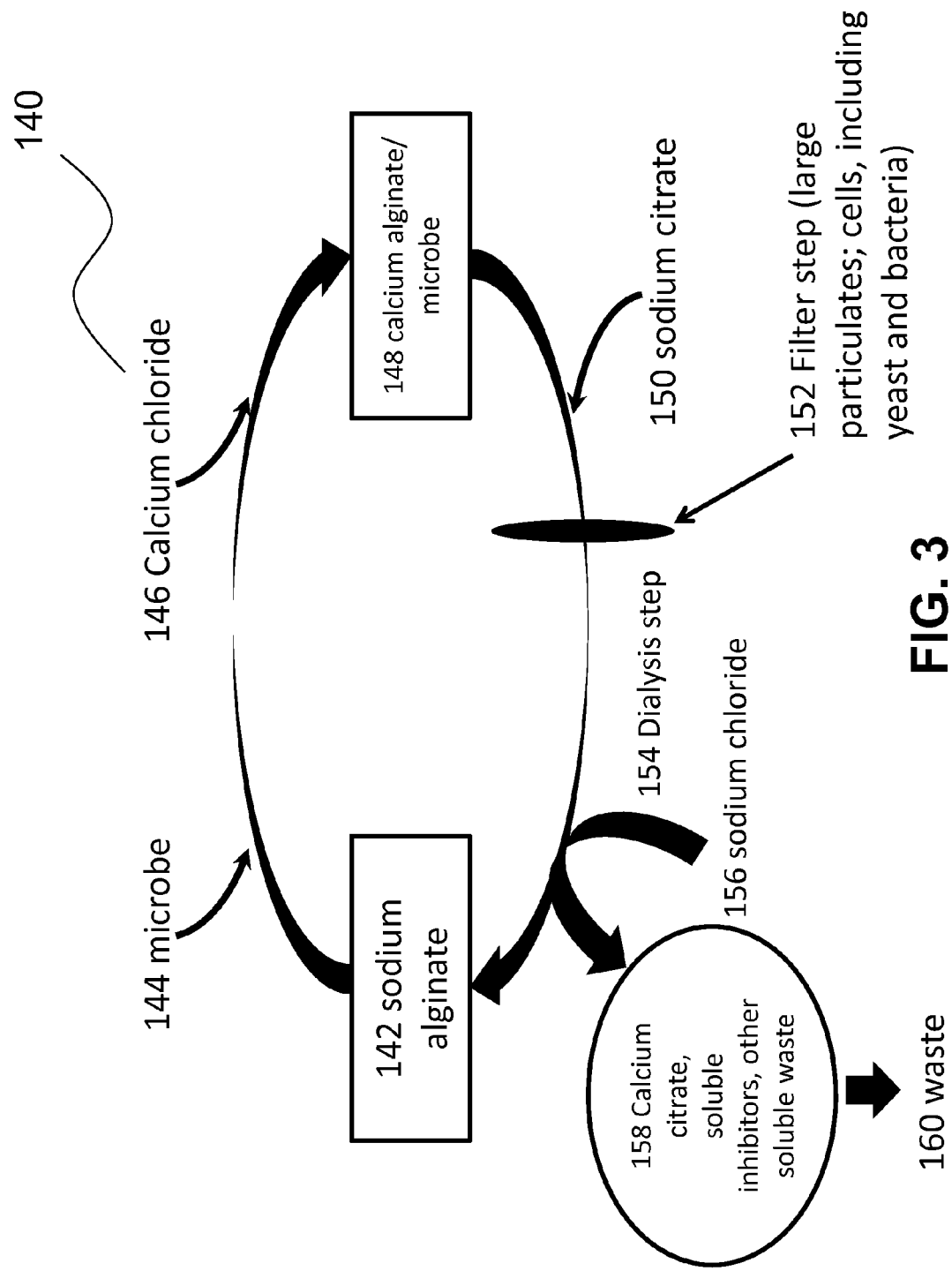
FIG. 3 illustrates a process for recycling a calcium alginate immobilization medium.

FIG. 3 illustrates a process 140 for recycling calcium alginate used in the microbe immobilization process. For example, in the case of *Pachysolen tannophilus* immobilized in calcium alginate beads, the calcium alginate from the beads used to immobilize the microbes may be recovered and recycled using process 140. In process 140, the degraded microbe/calcium alginate mixture 148, is dissociated with a calcium chelator complexed with a monovalent ion 150, such as sodium citrate or potassium citrate. Step 150 of process 140 dissociates the alginate and liberates the microbes (bacteria or yeast cells). In one preferred embodiment of process 140, step 150 is accomplished by stirring the microbe/calcium alginate mixture in 20 g/L sodium citrate or potassium citrate with a pH 8.2. at room temperature for 15 minutes.

Once the microbes have been liberated and the alginate dissociated, the solution is filtered to remove the large particulate and microbes (bacteria or yeast cells) in step 152.

The filtered solution is then dialyzed, step 154, against a sodium salt 156, such as sodium chloride, to remove the calcium citrate, extractives, and soluble microbial inhibitors 158. The resulting dialysis of the filtered solution with an inorganic salt, such as sodium chloride, regenerates sodium alginate. The toxic materials are removed as waste stream 160. The sodium alginate is concentrated during dialysis and then used again to produce calcium alginate in steps 142, 144, and 146 as described above. In one preferred embodiment, the sodium alginate is used to immobilize *Pachysolen tannophilus* in calcium alginate beads as taught in the above process.

In addition to the use in processes specifically designed to produce an alcohol, such as ethanol, the processes of the present patent document may be used in conjunction with other processes. For example, the paper-pulping process usually burns or discards the hemicellulose portion of the biomass. Using the processes taught herein, however, the hemicellulose may be separated and removed from the biomass and processed into ethanol, or other biofuel. Accordingly, the processes of the present patent document provide an efficient, cost-effective means for converting hemicellulose into ethanol, or other biofuels, in the paper-pulping, and other, industries. As a further non-limiting example, the processes disclosed in the present patent document may also be used to ferment monosaccharides, both hexose and pentose, obtained from the saccharification of sugarcane bagasse.

The following discussion will now be directed to bioreactors designed for use with immobilized microbes and in particular with immobilized *Pachysolen tannophilus.*

Fermentation may occur using a number of methods. Preferably the biomass hydrolysate is removed and fermented ex-situ. A variety of bioreactor designs, including a traditional non-stirred fermenter or stirred fermenter, may be used for the fermentation of the biomass hydrolysate using immobilized microbes. The reactor may be a submerged reactor or other type of liquid reactor. In order to provide the highest yield, a submerged reactor is preferable to ferment five-carbon sugars.

In the case of microbes that are immobilized, a packed bed reactor could be utilized, or a tankage system similar to that employed for carbon-in-pulp processes in the gold mining industry could be used. In the latter, beads would be moved counter-current to the solution flow and could be easily recovered for regeneration. Thin film reactors may also work well with immobilized microbes.

In addition, solid/liquid contactors may be used with immobilized microbes. These types of reactors include ion exchange columns, packed bed reactors, trickle flow reactors, and rotating contactors. Other reactors that may be used are fluidized-bed and upflow type reactors.

If the entrapment method of immobilization is used, the microbes may be incorporated into a bioreactor using a number of different methods. In addition to beads, the matrix/microbe gel may be applied to a support structures to increase the effective surface area. These configurations may include coating paddle structures, used in stirred tank reactors, rotating contactors, and thin film reactors. The microbes could also be incorporated in large three-dimensional open-cell supports for use in trickle flow reactors or fluidized-bed and upflow reactors.

Figure 4:
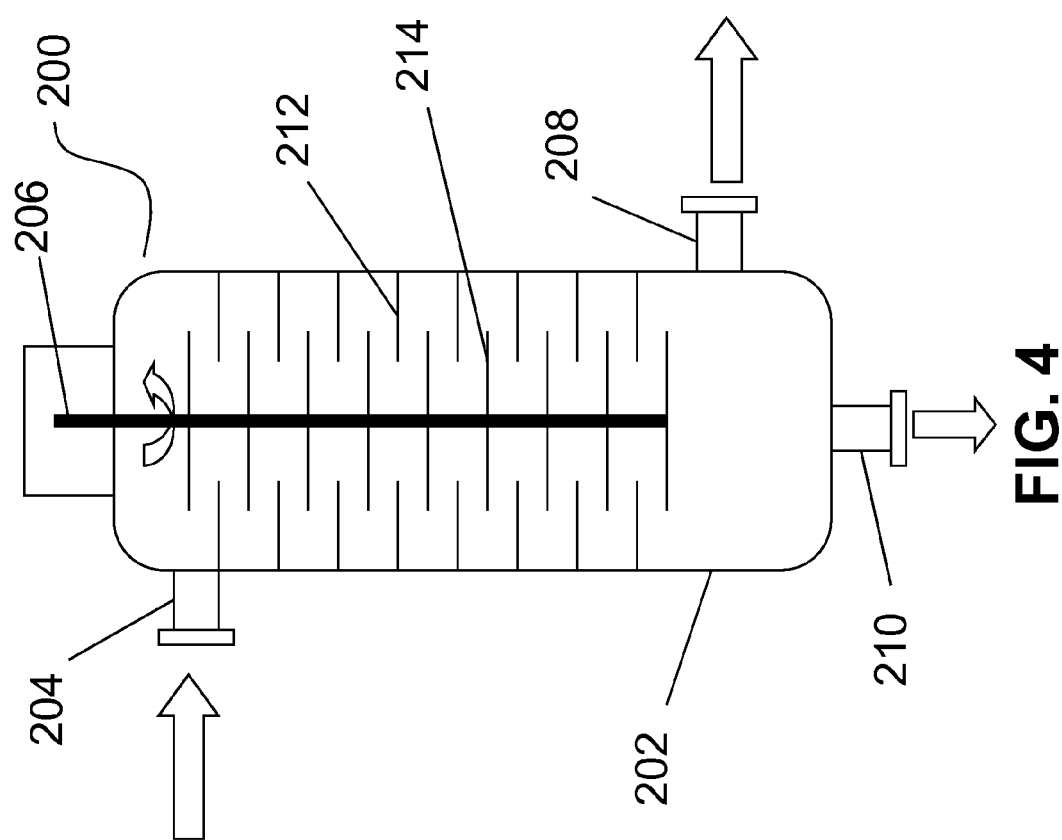
FIG. 4 illustrates a view of one embodiment of a bioreactor for performing submerged fermentation of biomass hydrolysate using immobilized microbes.

FIG. 4 illustrates a view of one embodiment of a bioreactor for performing submerged fermentation of biomass hydrolysate using immobilized microbes. Bioreactor 200, which may be referred to as a rotating disk contactor, comprises vessel 202, input 204, rotating stir stick 206, outputs 208 and 210, stators 212, and rotors 214.

Although vessel 202 is shown in a vertical configuration it may also be horizontal or in some other orientation. Vessel 202, preferably includes a large opening. For example, vessel 202 may be made of two separable halves in order to facilitate maintenance access to the stators 212 or rotors 214 located within vessel 202.

In a preferred embodiment, microbes immobilized in a matrix substance, such as calcium alginate, are applied to the stators 212 and the rotors 214. With this structure biomass hydrolysate flows through the vessel 202 from input 204 and through outputs 208 and 210. While the biomass is flowing, the rotating stir stick 206 may be rotated to provide agitation to the biomass hydrolysate as it flows through the bioreactor 200. Preferably the bioreactor 200 is designed for continuous flow fermentation.

Figure 5:
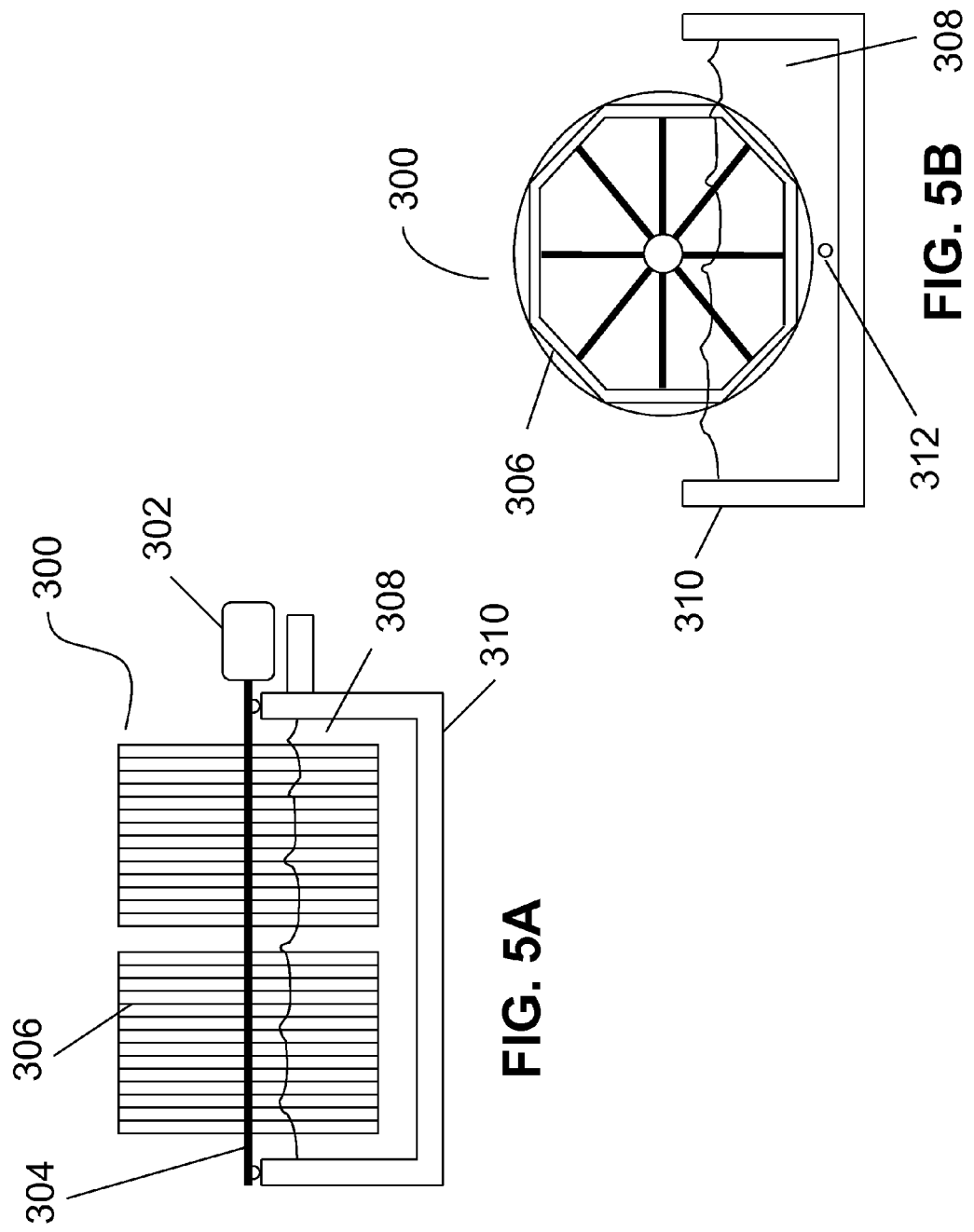
FIG. 5A illustrates a side view of another embodiment of a bioreactor for performing submerged fermentation of biomass hydrolysate using immobilized microbes.
FIG. 5B illustrates a front view of the bioreactor shown in FIG. 5A.

FIG. 5A and FIG. 5B illustrates a side and front view of another embodiment of a bioreactor for performing submerged fermentation of biomass hydrolysate using immobilized microbes. Bioreactor 300, comprises motor 302, rotating shaft 304, media disk panels 306, biomass hydrolysate 308, vessel 310, and optional air tube 312. Biomass hydrolysate 308, is added to the bioreactor 300 for fermentation.

Vessel 302 of bioreactor 300 is shown as only a bottom half, but vessel 302 may completely encapsulate the rotating media disks 306. In a preferred embodiment, microbes immobilized in a matrix substance may be applied to the media disk panels 306. Motor 302 rotates the media disks 306 through the biomass hydrolysate 308.

In one embodiment, bioreactor 300 includes an optional air tube 312 that may be used to further agitate the biomass hydrolysate 308 and increase fermentation by injecting air below the rotating media disk panels 306.

Figure 6:
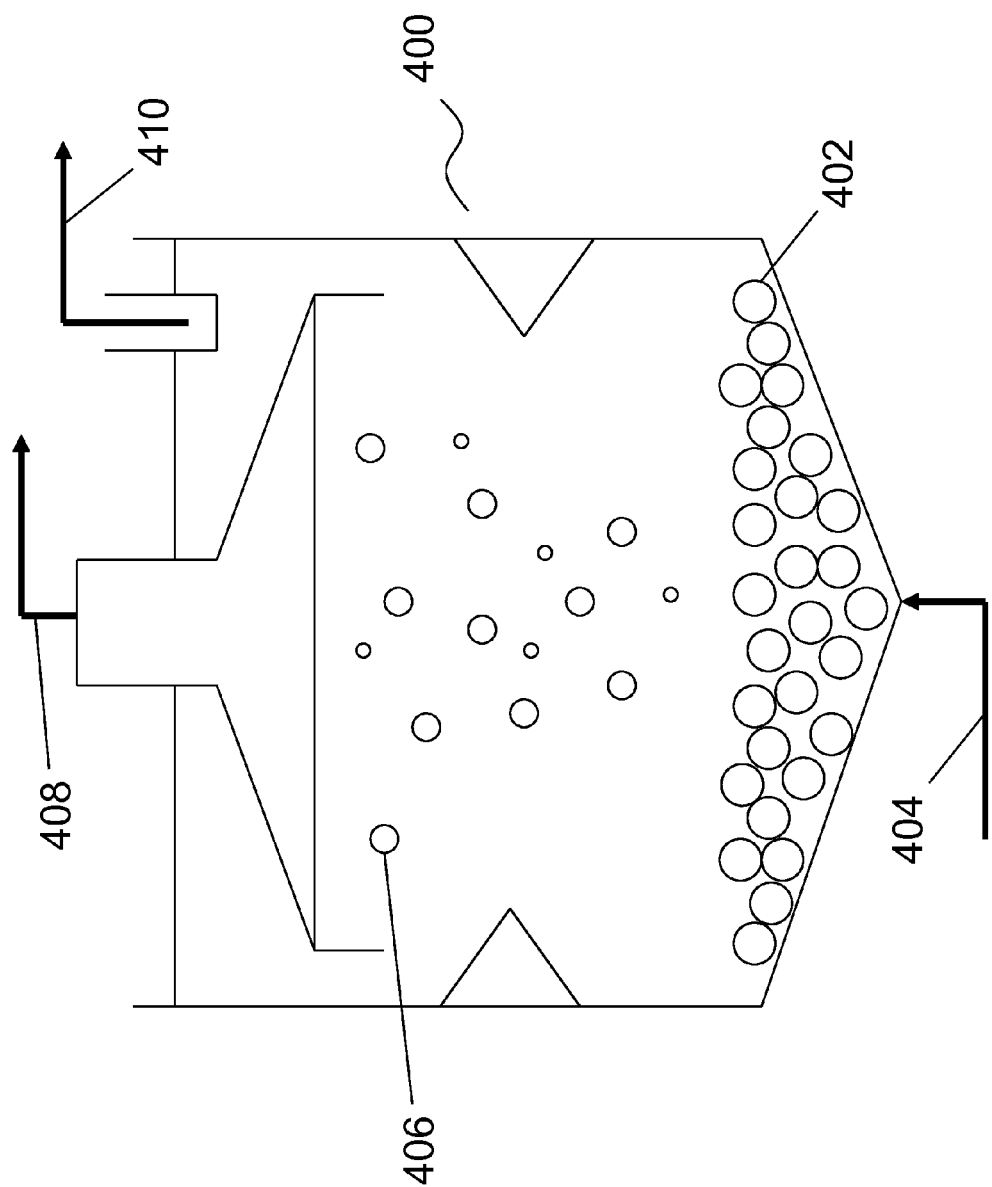
FIG. 6 illustrates an up-flow reactor for performing submerged fermentation of biomass hydrolysate using immobilized microbes.

FIG. 6 illustrates an upflow reactor. Upflow reactor 400 contains sludge bed or sludge blanket 402. For use to ferment biomass hydrolysate, sludge bed 402 comprises immobilized microbes. Sludge bed 402 may be comprised of one or more fermented microbes immobilized in any of the various medium described above. For example, sludge bed 402 may be comprised of *Pachysolen tannophilus* immobilized in calcium alginate beads. Upflow reactor 402 further comprises inlet(s) 404 for influent. Inlet(s) 404 may be a single inlet or more preferably a plurality of inlets across the bottom of the upflow reactor 400 to distribute the influent evenly underneath the sludge bed 402. Inlet(s) 404 allow the biomass hydrolysate to enter the upflow reactor from beneath the sludge bed 402. As the biomass hydrolysate is fermented, biogas 406 rises to the surface of the reactor and is collected at the top 408 of the upflow reactor 400. Effluent 410 is removed from the reactor and recycled through the inlet(s) 404.

Preferably the upflow reactor 400 is a columnar upflow reactor with a low aspect ratio between the range of about 1:1 to 2:1 height to width. Carbon dioxide gas produced by the fermentation process disrupts the packing of the beads loaded in the column and promotes a 'self-fluidizing' bed, similar to the effect achieved by a gas-lift type of reactor.

In a preferred embodiment, two or more 'self-fluidizing' bed columnar upflow reactors 400 can be run in series. The beads in each reactors may contain the same or different microbes, so as to ferment different sugars in different reactor stages. An increase in the number of reactors placed in series will reduce the sugar/ethanol variation within any given reactor, which in turn will promote better microbe performance.

In addition to the bioreactor designs shown in FIG. 4, FIG. 5A, 5B, and FIG. 6, it is to be understood that numerous other submerged or contact bioreactor designs may be used with the processes taught herein.

Bioreactors based on immobilized microbes offer several advantages over 'free cell' systems. One advantage is the increased feasibility to employ a continuous fermentation system. Immobilization ensures no loss of cell mass, such as occurs with batch fermentation and with continuous fermentation where the flow rate is such that the free cells are washed out of the reactor with the product. Continuous fermentation also decreases production down-time compared to batch fermentation. Continuous fermentation using microbes immobilized in beads increases the flow rate and the ethanol productivity possible with, for example, an upflow reactor. Immobilization also ensures no loss of cell mass of motile cells, where the flow rate is either high or low, where the inherent motility of the cell leads to loss of cell mass.

The following example demonstrates the application of one embodiment of the present patent document applied to beetle-killed pine. For the purposes of the present example *Pachysolen tannophilus* was either immobilized in calcium alginate beads with about a 3 mm diameter (generated using the method describe above) or was in a free cell state. Tables 3 and 4 below summarize the improvement of ethanol yield, and in glucose and xylose conversion resulting from the reactor design employed according to the present example.

The present example demonstrates the improvement of ethanol yield, and in glucose and xylose conversion, for calcium alginate-immobilized *Pachysolen tannophilus* in two different softwood hydrolysates ('A' and 'B') over free (i.e. unrestricted) *Pachysolen tannophilus*. The hydrolysates were pH adjusted or overlimed and pH adjusted. The *Pachysolen tannophilus* strain NRRL Y2460 was used in carrying out the experiment; however, other adapted or mutated strains of *Pachysolen tannophilus* may also be immobilized in calcium alginate and used in processes according to the present patent document.

The pine was transformed into a softwood hydrolysate by dilute acid hydrolysis. The hydrolysate was either simply pH adjusted with sodium hydroxide or 'overlimed'. As mentioned above overliming with calcium hydroxide is commonly used to ameliorate the toxicity of hydrolysates. The resulting solutions were fermented using *Pachysolen tannophilus* immobilized in 3 mm calcium alginate beads.

The beads were incubated in a flask of Yeast Peptone Dextrose (YPD) broth for 22 hours at 30° C. and 75 rpm. YPD is a standard yeast medium containing 10 g/L yeast extract, 20 g/L peptone, and 20 g/L dextrose. Similarly, the free cells were cultured from a working slant into a flask of YPD broth and incubated for 24 hours at 30° C. and 75 rpm.

To prepare the pH adjusted hydrolysate, the solution was adjusted to pH 6.0 with 8M potassium hydroxide, followed by filter sterilization. Preparation of overlimed and pH adjusted hydrolysate required overliming to pH 10.0 with calcium oxide, followed by a 30 minute hold at 50° C. under stirring conditions. The overlimed hydrolysate was then filtered to remove the solids. Following re-acidification to pH 6.0, the hydrolysate was filter sterilized.

Serum vials were aseptically prepared to obtain a final concentration of 95% hydrolysate with the following nutrient additions: 0.2% urea w/v, 0.2% yeast extract, and 0.05% potassium dihydrogen phosphate. The inoculation rate for immobilized beads was 0.2 g beads per mL. Following rinsing and re-suspension in sterile buffer, the free cells were inoculated at a rate of 0.3 $OD_{600nm}$ per mL. All experimental conditions were set up in triplicate serum vials. The vials were aseptically vented and incubated for 72 hours at 30° C. and 75 rpm prior to sampling for analysis.

In pH adjusted hydrolysate "A", as shown in Table 3, 'free' *Pachysolen* was unable to convert sugars to ethanol and no xylose was utilized. Immobilized *Pachysolen* converted most of the sugars (81%) to ethanol and converted 51% of the xylose. The data shows that immobilization greatly increased the ability of *Pachysolen* to overcome the inhibitory effects of the toxic compounds contained in the pH adjusted hydrolysate.

In overlimed hydrolysate "A", as reflected in Table 3, 'free' *Pachysolen* converted 60% of sugars to ethanol, and immobilized *Pachysolen* 86% of sugars. Xylose utilization was 0% for free cells. This is a surprising result with respect to reports in the current literature that *Pachysolen tannophilus* will ferment pentoses, and particularly xylose, in a defined medium. It is the inventors' hypothesis that despite removal of detectable levels of HMF and furfural by overliming, significant amounts of other inhibitors, discussed above, or combinations thereof still remain in the hydrolysate thus preventing fermentation. When the *Pachysolen tannophilus* was immobilized xylose utilization jumped to 76%. Immobilization thus enhances the benefit of overliming and greatly increases xylose utilization.

Table 4 shows similar results to Table 3. In pH adjusted hydrolysate "B", as shown in Table 4, 'free' *Pachysolen* was unable to convert sugars to ethanol and no xylose was utilized. Immobilized *Pachysolen* converted a majority of the sugars (57%) to ethanol.

Moreover, as reflected in Table 4, in overlimed hydrolysate "B" that contained very high inhibitor concentrations, 'free' *Pachysolen* was unable to ferment available sugars, while immobilized *Pachysolen* fermented 83% of available sugars, including xylose, to ethanol.

TABLE 3

Softwood hydrolysate 'A' fermentation characteristics with *Pachysolen tannophilus*

| | pH adjusted | | | | | Overlimed and pH adjusted | | | | |
|---|---|---|---|---|---|---|---|---|---|---|
| | Ethanol yield (%) | Sugar Utilization (%) | | Solution Inhibitors (g/L) | | Ethanol yield (%) | Sugar Utilization (%) | | Solution Inhibitors (g/L) | |
| Cells | theoretical† | glucose | xylose | furfural | HMF | theoretical† | glucose | xylose | furfural | HMF |
| Free | 0.0% | 0.0% | 0.0% | 0.42 | 4.03 | 61.8% | 72.2% | 0.0% | <DL | <DL |
| | | | | | | 57.4% | 75.8% | 0.0% | | |
| Imm. | 81.3% | 65.2% | 51.1% | 0.42 | 4.03 | 79.7% | 61.6% | 79.3% | <DL | <DL |
| | | | | | | 92.7% | 67.9% | 73.4% | | |

†Glucose concentration: 13.5 g/L; Xylose concentration: 3.4 g/L
DL = Detectable Limit;
Imm. = Immobilized

TABLE 4

Softwood hydrolysate 'B' fermentation characteristics with *Pachysolen tannophilus*

| | pH adjusted | | | | | Overlimed and pH adjusted | | | | |
|---|---|---|---|---|---|---|---|---|---|---|
| | Ethanol yield (% | Sugar Utilization (%) | | Solution Inhibitors (g/L) | | Ethanol yield (% | Sugar Utilization (%) | | Solution Inhibitors (g/L) | |
| Cells | theoretical)† | glucose | xylose | furfural | HMF | theoretical)† | glucose | xylose | furfural | HMF |
| Free | 0.0% | 0.0% | 0.0% | 5.91 | 1.32 | 0.0% | 0.0% | 0.0% | 1.04 | 0.79 |
| Imm | 56.9% | 35.7% | 15.9% | 5.91 | 1.32 | 83.3% | 53.8% | 73.0% | 1.04 | 0.79 |

†Glucose concentration: 4.7 g/L; Xylose concentration: 3.2 g/L
Imm. = Immobilized In the preceding example summarized in Tables 3 and 4, and the subsequent examples in Tables 5-7 below, ethanol yield (% theoretical) is based on glucose and xylose only and is calculated from total glucose and xylose concentrations before treatment. Other monosaccharides are not considered. All sugar utilization data is calculated using YSI results for glucose and xylose. Sugar utilization calculations do not differentiate between end products (i.e., includes ethanol, xylitol, biomass) and is calculated as follows (accounting for lost sugars after treatment like overliming, autoclaving, etc.):

For Hydrolysate Calculations:

$$\% \text{ Sugar} \times \text{Conversion} = \frac{NS - RS}{TS} * 98$$

NS=Sugar×Concentration after Treatment (i.e., Negative Control)
RS=Residual Sugar×Concentration after Fermentation
TS=Total Sugar×Concentration before Treatment Other embodiments of the processes taught in the present patent document will include using different microbes and different conditioning methods. For example, Tables 5 and 6 illustrate the improvement in ethanol yield, and in glucose and xylose conversion, for calcium alginate-immobilized *Zymomonas mobilis* NREL strain 8b, *Pachysolen tannophilus* (NRRL Y2460), and *Pichia stipitis* (NRRL Y7124) in sugarcane hydrolysate over free cells of the same. Similar to the examples in tables 3 and 4, pH adjusted hydrolysate was compared against another conditioning method for both free and immobilized microbes. In contrast to the examples illustrated in tables 3 and 4, the hydrolysate used for the examples shown in tables 5-7 used hydrolysate derived from sugarcane bagasse instead of hydrolysate derived from softwood. Tables 5 and 6 illustrate the benefit of immobilization on a variety of microbes including both yeasts and bacterium.

The effects of the different conditioning steps on the concentrations of secondary inhibitory products are shown in Table 7. As shown in Table 7, the hydrolysates were conditioned by pH adjustment or by passing the hydrolysate over activated carbon (AC), strong acid ion exchange (IE) resin and weak base ion exchange resin, a treatment hereafter termed AC/IE.

TABLE 5

Percent conversion of glucose and xylose to ethanol.

| Strain | Cells | pH adjustment | AC/IE |
|---|---|---|---|
| Z. mobilis, NREL 8b | Imm. | 31.4 ± 0.9 | 71.4 ± 1.0 |
| | Free | 22.1 ± 0.7 | 32.4 ± 1.4 |
| P. tannophilus | Imm. | 24.8 ± 0.6 | 63.6 ± 0.4 |
| | Free | 5.7 ± 0.3 | 50.0 ± 0.2 |
| P. stipitis | Imm. | 11.9 ± 0.3 | 54.4 ± 0.7 |
| | Free | 4.1 ± 0.1 | 56.4 ± 2.1 |

Imm. = Immobilized

TABLE 6

Percent xylose utilized in 6 day fermentation.

| Strain | Cells | pH adjustment | AC/IE |
|---|---|---|---|
| Z. mobilis, NREL 8b | Imm. | 30.8 ± 0.7 | 75.1 ± 0.4 |
| | Free | 17.5 ± 0.0 | 17.6 ± 3.2 |
| P. tannophilus | Imm. | 23.7 ± 1.7 | 95.8 ± 0.5 |
| | Free | 11.5 ± 0.7 | 55.9 ± 4.3 |
| P. stipitis | Imm. | 16.4 ± 3.1 | 67.3 ± 1.9 |
| | Free | N.D. | 61.7 ± 3.0 |

N.D.—not detected;
Imm.—Immobilized;

TABLE 7

Inhibitor Concentrations in differently conditioned hydrolysates.

| Conditioning | Acetic acid (g/L) | Formic acid (g/L) | 5-HMF (g/L) | Furfural (g/L) |
|---|---|---|---|---|
| pH adjustment | 10.7 | 3.8 | 1.1 | 3.5 |
| AC/ion exchange | 0.1 | 0.4 | N.D. | N.D. |

N.D.—Not Detected.

The examples of Table 5-7 were conducted by transforming sugarcane bagasse into a bagasse hydrolysate by dilute acid hydrolysis. The hydrolysate was conditioned by either simply pH adjusting with sodium hydroxide or by treating the hydrolysate with activated carbon and the two ion exchange resins mentioned above. Namely, the bagasse hydrolysate was passed over a column containing activated carbon, over a column containing a strong acid cation exchange column, and a weak base anion exchange column. The resulting solutions were further separated into three separate solutions each to be fermented by three different microbes, *Zymomonas mobilis* NREL strain 8b, *Pachysolen tannophilus* (NRRL Y2460), and *Pichia stipitis* (NRRL Y7124) respectively. For each of the microbe solutions, two separate examples were performed, one with the microbe immobilized in 2-3 mm calcium alginate beads, and the other using free microbes. Consequently, there were four different fermentations for each microbe resulting in 12 total fermentations. Two fermentations with the microbe immobilized, one with a pH adjusted solution and one with an AC/IE conditioned solution and two fermentations using free microbes, one with a pH adjusted solution and one with an AC/IE conditioned solution.

The two differently-conditioned bagasse hydrolysates contained different amounts of the inhibitors acetic acid, formic acid, 5-hydroxyfurfural (5-HMF), and furfural. The measured values are reported in Table 7. These inhibitor levels are for the particular batch of sugarcane bagasse hydrolysate used in the experiments summarized above for which the results are reported in Tables 5 and 6.

The beads used for immobilizing the different microbes were incubated in a flask of Yeast Peptone Dextrose (YPD) broth for 22 hours at 30° C. and 75 rpm. Similarly, the free cells were cultured from a working slant into a flask of YPD broth and incubated for 24 hours at 30° C. and 175 rpm.

Serum vials were aseptically prepared to obtain a final concentration of 95% hydrolysate with the following nutrient additions: 0.2% urea w/v, 0.2% yeast extract, and 0.05% potassium dihydrogen phosphate. The inoculation rate for beads was 0.2 g beads per mL. Following rinsing and re-suspension in sterile buffer, the free cells were inoculated at a rate of 0.01 g (wet weight) per mL for *P. tannophilus* and *P. stipitis*, and 0.006 g (wet weight) per mL for *Z. mobilis* 8b. All experimental conditions were set up in triplicate serum vials. The vials were aseptically vented and incubated for 6 days at 30° C. and 75 rpm prior to sampling for analysis.

For sugarcane bagasse hydrolysate conditioned by pH adjustment, 'free' *Zymomonas* was able to convert 22% of the glucose and xylose to ethanol, while immobilized *Zymomonas* converted 31% (Table 5). Similarly, 'free' *Pachysolen* was able to convert 6% of the glucose and xylose to ethanol, while immobilized *Pachysolen* converted 25%, and 'free' *Pichia* was able to convert 4% of the glucose and xylose to ethanol, while immobilized *Pichia* converted 12% (Table 5). The data shows that immobilization greatly increased the ability of *Zymomonas, Pachysolen*, and *Pichia* to overcome the inhibitory effects of the toxic compounds contained in the pH adjusted bagasse hydrolysate (Table 5).

In AC/IE conditioned bagasse hydrolysate, as reflected in Table 5, 'free' *Zymomonas* was able to convert 32% of the glucose and xylose to ethanol, while immobilized *Zymomonas* converted 71%. Similarly, 'free' *Pachysolen* was able to convert 50% of the glucose and xylose to ethanol, while immobilized *Pachysolen* converted 64%. Unlike *Zymomonas* and *Pachysolen*, immobilized *Pichia* was actually less effective at converting glucose and xylose to ethanol than 'free' *Pichia*. As shown in Table 5, 'free' *Pichia* was able to convert 56% of the glucose and xylose to ethanol, while immobilized *Pichia* converted 54%. The data shows that immobilization greatly increased the ability of *Zymomonas* and *Pachysolen* to overcome the inhibitory effects of the toxic compounds contained in the AC/IE conditioned bagasse hydrolysate.

Xylose utilization in the fermentations generally mirrored the extent of fermentation of glucose and xylose to ethanol. Immobilized *Zymomonas* utilized 31% of xylose in pH adjusted hydrolysate and 75% in AC/IE conditioned hydrolysate, while the free cells utilized only 18% of the xylose in both conditions (Table 6). Immobilized *Pachysolen* utilized 24% of xylose in pH adjusted hydrolysate and 96% in AC/IE conditioned hydrolysate, while the free cells utilized only 12% and 56% of the xylose, respectively (Table 6). Immobilized *Pachysolen* utilized 25% of xylose in pH adjusted hydrolysate and 64% in AC/IE conditioned hydrolysate, while the free cells utilized only 6% and 50%, respectively. Immobilized *Pichia* utilized 16% of xylose in pH adjusted hydrolysate and 67% in AC/IE conditioned hydrolysate, while the free cells utilized no xylose in pH adjusted hydrolysate, but 62% in AC/IE conditioned hydrolysate (Table 6).

It is the inventors' hypothesis that despite removal of detectable levels of HMF and furfural and a great decrease in acetic and formic acids by AC/IE conditioning, significant amounts of other inhibitors, discussed above, and the remaining formic and acetic acids, or combinations thereof still remain in the hydrolysate thus interfering with fermentation. For *Zymomonas* and *Pachysolen*, immobilization increased xylose utilization significantly. Immobilization thus enhances the benefits of conditioning and greatly increases xylose utilization.

In another example of the processes taught in the present patent document, the microbe/calcium alginate beads were re-used in sequential fermentations and the microbes in the beads were metabolically 'regenerated' between fermentations to increase ethanol yield.

Figure 7:
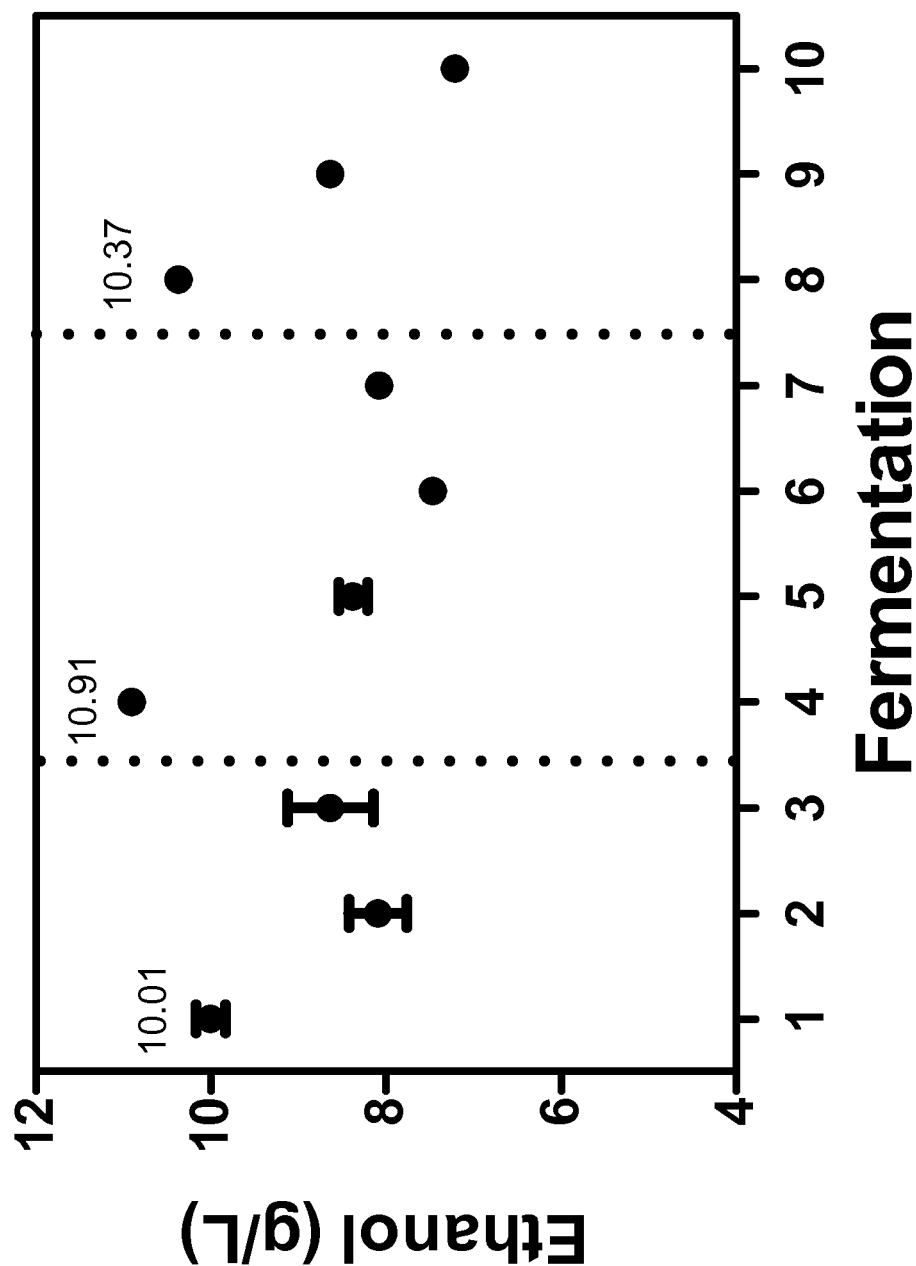
FIG. 7 is a graph illustrating ethanol yield of regenerated calcium alginate beads with immobilized fermentative microbes over a series of fermentations.

For the present example, fermentations using 2 g *Pachysolen*/calcium alginate beads per 10 ml softwood hydrolysate supplemented with 0.2% Urea, 0.2% Yeast Extract, and 0.05% $KH_2PO_4$ were performed at 30° C. and 75 rpm for 72 hours. After the fermentation reaction (Fermentation 1), the liquid was aseptically removed and analyzed for ethanol content, and the beads were aseptically rinsed several times with sterile deionized water. The same *Pachysolen*/calcium alginate beads were used in a second fermentation (Fermentation 2), in the same conditions, as Fermentation 1. Similarly, the fermentation liquid was subsequently analyzed and the beads rinsed. This was repeated for Fermentation 3. FIG. 7 illustrates the decreased ethanol yield in Fermentations 2 and 3 compared to Fermentation 1.

Next, the same *Pachysolen*/calcium alginate beads were regenerated between Fermentations 3 and 4 (shown as a dotted line in FIG. 7 between Fermentations 3 and 4) by incubating for 22 hours in a shaking incubator at 30° C. and 100 rpm in a yeast culture medium, Yeast Peptone Dextrose (YPD), after washing. The YPD was then aseptically removed and the beads were used in yet another fermentation (Fermentation 4). FIG. 7 illustrates that the regeneration of the *Pachysolen*/calcium alginate in culture medium restored the fermentative ability of the *Pachysolen* to produce ethanol.

Similar washes, fermentations, and a second regeneration (shown as a dotted line between fermentations 7 and 8) were performed using the same beads in another 6 fermentations. The results are shown in FIG. 7. FIG. 7 illustrates that immobilized microbes may be used in sequential fermentations and that the *Pachysolen* in the beads can be metabolically regenerated. Although the present example employs a regeneration step after 3 or 4 consecutive uses of the immobilized microbes, it is possible to regenerate the microbes more or less often. It is expected that if a greater number of beads are used in sequential fermentations (i.e. fermenting under conditions of a saturating yeast concentration), the ethanol yields would remain at a higher level in successive fermentations before requiring metabolic regeneration.

As discussed above, the immobilization medium, for example calcium alginate, can degrade due to use. If the microbes are regenerated and re-used according to the present example, it may be necessary to recycle the immobilization medium as taught above.

Although the invention has been described with reference to preferred embodiments and specific examples, it will readily be appreciated by those skilled in the art that many modifications and adaptations of the methods and bioreactors described herein are possible without departure from the spirit and scope of the invention as claimed hereinafter. Thus, it is to be clearly understood that this description is made only by way of example and not as a limitation on the scope of the invention as claimed below.

What is claimed is:

1. A process for converting biomass hydrolysate into biofuel, the process comprising the steps of:
   a. contacting a biomass hydrolysate solution comprising monosaccharides with an immobilized fermentative microbe strain immobilized in calcium alginate for a sufficient reaction time to convert monosaccharides in the biomass hydrolysate to biofuel;
   b. recovering biofuel from the fermented hydrolysate;
   c. recovering the calcium alginate;
   d. regenerating sodium alginate from the calcium alginate to obtain recycled sodium alginate; and
   e. immobilizing additional fermentative microbes using the recycled sodium alginate.

* * * * *